(12) United States Patent
Gonzalez et al.

(10) Patent No.: US 8,747,401 B2
(45) Date of Patent: Jun. 10, 2014

(54) SYSTEMS AND METHODS FOR TURBINATE REDUCTION

(75) Inventors: Lloyd Gonzalez, Austin, TX (US); Lona Foelker, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 758 days.

(21) Appl. No.: 13/010,454

(22) Filed: Jan. 20, 2011

(65) Prior Publication Data

US 2012/0191089 A1 Jul. 26, 2012

(51) Int. Cl.
*A61B 18/14* (2006.01)

(52) U.S. Cl.
USPC .......................................................... 606/41

(58) Field of Classification Search
USPC ............................................ 606/27, 34, 41
See application file for complete search history.

(56) References Cited

U.S. PATENT DOCUMENTS

| | | | |
|---|---|---|---|
| 2,050,904 A | 8/1936 | Talley | 219/233 |
| 2,056,377 A | 10/1939 | Wappler | 125/303 |
| 3,633,425 A | 1/1972 | Sanford | 73/356 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |

(Continued)

FOREIGN PATENT DOCUMENTS

| | | | | |
|---|---|---|---|---|
| DE | 3930451 A1 | 3/1991 | | A61B 17/39 |
| EP | 0509670 | 10/1992 | | A61B 17/39 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Michael Peffley
*Assistant Examiner* — Daniel Fowler
(74) *Attorney, Agent, or Firm* — Matthew Scheele; Brian E. Szymczak

(57) ABSTRACT

The present disclosure includes an electrosurgical apparatus for treating tissue at a target site. The apparatus has a shaft with a proximal end and a distal end, and the distal end includes an active disposed laterally on the shaft distal end and return electrode. The return electrode may have a plurality of apertures through it, which are fluidly connected to a fluid delivery element, operable to deliver a conductive fluid to the shaft distal end. The return electrode may encircle at least a portion of the shaft and may extend distally and proximally from the active electrode.

30 Claims, 12 Drawing Sheets

(56) References Cited

U.S. PATENT DOCUMENTS

| | | | | |
|---|---|---|---|---|
| 4,232,676 A | 11/1980 | Herczog | | 128/303 |
| 4,248,231 A | 2/1981 | Herczog et al. | | 128/303 |
| 4,301,802 A | 11/1981 | Poler | | 606/48 |
| 4,326,529 A | 4/1982 | Doss et al. | | 128/303 |
| 4,381,007 A | 4/1983 | Doss | | 128/303 |
| 4,474,179 A | 10/1984 | Koch | | 606/40 |
| 4,476,862 A | 10/1984 | Pao | | 128/303 |
| 4,532,924 A | 8/1985 | Auth et al. | | 128/303 |
| 4,548,207 A | 10/1985 | Reimels | | 128/303 |
| 4,567,890 A | 2/1986 | Ohta et al. | | 128/303 |
| 4,582,057 A | 4/1986 | Auth et al. | | 606/31 |
| 4,590,934 A | 5/1986 | Malis et al. | | 128/303 |
| 4,593,691 A | 6/1986 | Lindstrom et al. | | 128/303 |
| 4,658,817 A | 4/1987 | Hardy | | 606/14 |
| 4,660,571 A | 4/1987 | Hess et al. | | 128/784 |
| 4,674,499 A | 6/1987 | Pao | | 128/303 |
| 4,682,596 A | 7/1987 | Bales et al. | | 128/303 |
| 4,706,667 A | 11/1987 | Roos | | 128/303 |
| 4,709,698 A | 12/1987 | Johnston et al. | | 606/41 |
| 4,727,874 A | 3/1988 | Bowers et al. | | 128/303 |
| 4,765,331 A | 8/1988 | Petruzzi et al. | | 128/303 |
| 4,785,823 A | 11/1988 | Eggers et al. | | 128/692 |
| 4,805,616 A | 2/1989 | Pao | | 128/303 |
| 4,823,791 A | 4/1989 | D'Amelio et al. | | 123/303 |
| 4,832,048 A | 5/1989 | Cohen | | 128/786 |
| 4,860,752 A | 8/1989 | Turner | | 607/102 |
| 4,907,589 A | 3/1990 | Cosman | | 606/34 |
| 4,920,978 A | 5/1990 | Colvin | | 128/784 |
| 4,931,047 A | 6/1990 | Broadwin et al. | | 604/22 |
| 4,936,281 A | 6/1990 | Stasz | | 128/660 |
| 4,936,301 A | 6/1990 | Rexroth et al. | | 606/45 |
| 4,943,290 A | 7/1990 | Rexroth et al. | | 606/45 |
| 4,966,597 A | 10/1990 | Cosman | | 606/50 |
| 4,967,765 A | 11/1990 | Turner et al. | | 128/785 |
| 4,976,711 A | 12/1990 | Parins et al. | | 606/48 |
| 4,979,948 A | 12/1990 | Geddes et al. | | 606/33 |
| 4,998,933 A | 3/1991 | Eggers et al. | | 606/41 |
| 5,007,908 A | 4/1991 | Rydell | | 606/47 |
| 5,009,656 A | 4/1991 | Reimels | | 606/48 |
| 5,035,696 A | 7/1991 | Rydell | | 606/47 |
| 5,047,026 A | 9/1991 | Rydell | | 606/48 |
| 5,047,027 A | 9/1991 | Rydell | | 606/48 |
| 5,057,105 A | 10/1991 | Malone et al. | | 606/28 |
| 5,057,106 A | 10/1991 | Kasevich et al. | | 606/33 |
| 5,078,716 A | 1/1992 | Doll | | 606/47 |
| 5,078,717 A | 1/1992 | Parins et al. | | 606/48 |
| 5,080,660 A | 1/1992 | Buelna | | 606/45 |
| 5,083,565 A | 1/1992 | Parins | | 600/374 |
| 5,084,044 A | 1/1992 | Quint | | 606/27 |
| 5,085,659 A | 2/1992 | Rydell | | 606/47 |
| 5,088,997 A | 2/1992 | Delahuerga et al. | | 606/42 |
| 5,098,431 A | 3/1992 | Rydell | | 606/48 |
| 5,099,840 A | 3/1992 | Goble | | 128/422 |
| 5,102,410 A | 4/1992 | Dressel | | 606/15 |
| 5,108,391 A | 4/1992 | Flachenecker et al. | | 606/38 |
| RE33,925 E | 5/1992 | Bales et al. | | 606/48 |
| 5,112,330 A | 5/1992 | Nishigaki et al. | | 606/46 |
| 5,122,138 A | 6/1992 | Manwaring | | 606/46 |
| 5,125,928 A | 6/1992 | Parins et al. | | 606/48 |
| 5,156,151 A | 10/1992 | Imran | | 600/375 |
| 5,167,659 A | 12/1992 | Ohtomo et al. | | 606/40 |
| 5,167,660 A | 12/1992 | Altendorf | | 606/40 |
| 5,171,311 A | 12/1992 | Rydell et al. | | 606/48 |
| 5,178,620 A | 1/1993 | Eggers et al. | | 606/41 |
| 5,190,517 A | 3/1993 | Zieve et al. | | 604/22 |
| 5,192,280 A | 3/1993 | Parins | | 606/48 |
| 5,195,959 A | 3/1993 | Smith | | 604/34 |
| 5,195,968 A | 3/1993 | Lundquist et al. | | 604/95.04 |
| 5,196,007 A | 3/1993 | Ellman | | 606/32 |
| 5,197,466 A | 3/1993 | Marchosky et al. | | 128/399 |
| 5,197,963 A | 3/1993 | Parins | | 606/46 |
| 5,207,675 A | 5/1993 | Canady | | 606/40 |
| 5,217,457 A | 6/1993 | Delahuerga et al. | | 606/42 |
| 5,217,459 A | 6/1993 | Kamerling | | 606/48 |
| 5,249,585 A | 10/1993 | Turner et al. | | 607/99 |
| 5,261,410 A | 11/1993 | Alfano et al. | | 600/475 |
| 5,267,994 A | 12/1993 | Gentelia et al. | | 606/15 |
| 5,267,997 A | 12/1993 | Farin et al. | | 606/38 |
| 5,273,524 A | 12/1993 | Fox et al. | | 604/21 |
| 5,277,201 A | 1/1994 | Stern | | 607/98 |
| 5,281,216 A | 1/1994 | Klicek | | 606/42 |
| 5,281,218 A | 1/1994 | Imran | | 606/41 |
| 5,290,282 A | 3/1994 | Casscells | | 606/29 |
| 5,300,069 A | 4/1994 | Hunsberger et al. | | 606/37 |
| 5,306,238 A | 4/1994 | Fleenor | | 606/42 |
| 5,312,400 A | 5/1994 | Bales et al. | | 606/41 |
| 5,314,406 A | 5/1994 | Arias et al. | | 604/21 |
| 5,324,254 A | 6/1994 | Phillips | | 604/21 |
| 5,330,470 A | 7/1994 | Hagen | | 606/42 |
| 5,334,140 A | 8/1994 | Philips | | 604/35 |
| 5,334,183 A | 8/1994 | Wuchinich | | 606/46 |
| 5,334,193 A | 8/1994 | Nardella | | 606/41 |
| 5,336,220 A | 8/1994 | Ryan et al. | | 604/22 |
| 5,336,443 A | 8/1994 | Odashima | | 252/511 |
| 5,342,357 A | 8/1994 | Nardella | | 606/40 |
| 5,363,861 A | 11/1994 | Edwards et al. | | 600/585 |
| 5,366,443 A | 11/1994 | Eggers et al. | | 604/114 |
| 5,370,675 A | 12/1994 | Edwards et al. | | 607/101 |
| 5,374,261 A | 12/1994 | Yoon | | 604/385.01 |
| 5,375,588 A | 12/1994 | Yoon | | 128/4 |
| 5,380,277 A | 1/1995 | Phillips | | 604/33 |
| 5,380,316 A | 1/1995 | Aita | | 606/7 |
| 5,383,876 A | 1/1995 | Nardella | | 606/49 |
| 5,383,917 A | 1/1995 | Desai et al. | | 607/702 |
| 5,389,096 A | 2/1995 | Aita | | 606/15 |
| 5,395,312 A | 3/1995 | Desai | | 604/22 |
| 5,395,363 A | 3/1995 | Billings et al. | | 606/41 |
| 5,395,368 A | 3/1995 | Ellman et al. | | 606/45 |
| 5,400,267 A | 3/1995 | Denen et al. | | 702/59 |
| 5,401,272 A | 3/1995 | Perkins | | 606/15 |
| 5,403,311 A | 4/1995 | Abele et al. | | 606/49 |
| 5,417,687 A | 5/1995 | Nardella et al. | | 606/32 |
| 5,419,767 A | 5/1995 | Eggers et al. | | 604/114 |
| 5,423,810 A | 6/1995 | Goble et al. | | 606/40 |
| 5,423,811 A | 6/1995 | Imran et al. | | 606/41 |
| 5,423,812 A | 6/1995 | Ellman et al. | | 606/45 |
| 5,423,882 A | 6/1995 | Jackman et al. | | 607/122 |
| 5,436,566 A | 7/1995 | Thompson et al. | | 324/713 |
| 5,437,662 A | 8/1995 | Nardella | | 606/40 |
| 5,438,302 A | 8/1995 | Goble | | 331/167 |
| 5,441,499 A | 8/1995 | Fritzsch | | 606/45 |
| 5,451,224 A | 9/1995 | Goble et al. | | 606/48 |
| 5,454,809 A | 10/1995 | Janssen | | 606/41 |
| 5,456,662 A | 10/1995 | Edwards et al. | | 604/22 |
| 5,458,596 A | 10/1995 | Lax et al. | | 606/31 |
| 5,487,757 A | 1/1996 | Truckai et al. | | 604/264 |
| 5,490,850 A | 2/1996 | Ellman et al. | | 606/45 |
| 5,496,312 A | 3/1996 | Klicek | | 606/34 |
| 5,496,314 A | 3/1996 | Eggers | | 606/41 |
| 5,496,317 A | 3/1996 | Goble et al. | | 606/48 |
| 5,505,728 A | 4/1996 | Ellman et al. | | 606/39 |
| 5,505,730 A | 4/1996 | Edwards | | 606/41 |
| 5,514,130 A | 5/1996 | Baker | | 606/41 |
| 5,554,152 A | 9/1996 | Aita | | 606/7 |
| 5,556,397 A | 9/1996 | Long et al. | | 606/48 |
| 5,562,503 A | 10/1996 | Ellman et al. | | 439/638 |
| 5,562,703 A | 10/1996 | Desai | | 606/210 |
| 5,569,242 A | 10/1996 | Lax et al. | | 606/42 |
| 5,571,100 A | 11/1996 | Goble et al. | | 606/41 |
| 5,571,101 A | 11/1996 | Ellman et al. | | 606/45 |
| 5,584,872 A | 12/1996 | LaFontaine et al. | | 607/117 |
| 5,609,151 A | 3/1997 | Mulier et al. | | 128/642 |
| 5,624,439 A | 4/1997 | Edwards et al. | | 606/45 |
| 5,630,812 A | 5/1997 | Ellman et al. | | 606/41 |
| 5,633,578 A | 5/1997 | Eggers et al. | | 323/301 |
| 5,647,869 A | 7/1997 | Goble et al. | | 606/37 |
| 5,658,278 A | 8/1997 | Imran et al. | | 606/41 |
| 5,662,680 A | 9/1997 | Desai | | 606/210 |
| 5,674,191 A | 10/1997 | Edwards et al. | | 604/22 |
| 5,676,693 A | 10/1997 | LaFontaine et al. | | 607/116 |
| 5,681,282 A | 10/1997 | Eggers et al. | | 604/114 |
| 5,683,366 A | 11/1997 | Eggers et al. | | 604/114 |
| 5,683,386 A | 11/1997 | Ellman et al. | | 606/41 |
| 5,683,387 A | 11/1997 | Garito et al. | | 606/45 |

(56) References Cited

U.S. PATENT DOCUMENTS

| | | | | |
|---|---|---|---|---|
| 5,688,267 | A | 11/1997 | Panescu et al. | 606/41 |
| 5,695,495 | A | 12/1997 | Ellman et al. | 606/41 |
| 5,697,281 | A | 12/1997 | Eggers et al. | 604/114 |
| 5,697,536 | A | 12/1997 | Eggers et al. | 604/114 |
| 5,697,882 | A | 12/1997 | Eggers et al. | 604/114 |
| 5,697,909 | A | 12/1997 | Eggers et al. | 604/114 |
| 5,700,262 | A | 12/1997 | Acosta et al. | 606/48 |
| 5,707,349 | A | 1/1998 | Edwards | 604/22 |
| 5,718,702 | A | 2/1998 | Edwards | 606/41 |
| 5,725,524 | A | 3/1998 | Mulier et al. | 606/41 |
| 5,728,094 | A | 3/1998 | Edwards | 606/41 |
| 5,733,282 | A | 3/1998 | Ellman et al. | 606/45 |
| 5,738,114 | A | 4/1998 | Edwards | 128/898 |
| 5,743,870 | A | 4/1998 | Edwards | 604/22 |
| 5,746,224 | A | 5/1998 | Edwards | 128/898 |
| 5,749,869 | A | 5/1998 | Lindenmeier et al. | 606/34 |
| 5,766,153 | A | 6/1998 | Eggers et al. | 604/114 |
| 5,775,338 | A | 7/1998 | Hastings | 128/898 |
| 5,776,128 | A | 7/1998 | Eggers | 606/48 |
| 5,782,828 | A | 7/1998 | Chen et al. | 606/42 |
| 5,800,379 | A | 9/1998 | Edwards | 604/22 |
| 5,800,429 | A | 9/1998 | Edwards | 606/41 |
| 5,807,395 | A | 9/1998 | Mulier et al. | 606/41 |
| 5,810,764 | A | 9/1998 | Eggers et al. | 604/23 |
| 5,810,809 | A | 9/1998 | Rydell | 606/49 |
| 5,817,049 | A | 10/1998 | Edwards | 604/22 |
| 5,820,580 | A | 10/1998 | Edwards et al. | 604/22 |
| 5,823,197 | A | 10/1998 | Edwards | 128/898 |
| 5,827,277 | A | 10/1998 | Edwards | 606/41 |
| 5,836,875 | A | 11/1998 | Webster, Jr. | 600/374 |
| 5,843,019 | A | 12/1998 | Eggers et al. | 604/22 |
| 5,843,021 | A | 12/1998 | Edwards et al. | 604/22 |
| 5,843,077 | A | 12/1998 | Edwards | 606/41 |
| 5,860,951 | A | 1/1999 | Eggers | 604/510 |
| 5,860,974 | A | 1/1999 | Abele | 606/41 |
| 5,860,975 | A | 1/1999 | Goble et al. | 606/41 |
| 5,871,469 | A | 2/1999 | Eggers et al. | 604/114 |
| 5,873,855 | A | 2/1999 | Eggers et al. | 604/114 |
| 5,879,349 | A | 3/1999 | Edwards | 606/45 |
| 5,885,277 | A | 3/1999 | Korth | 606/35 |
| 5,888,198 | A | 3/1999 | Eggers et al. | 604/114 |
| 5,891,095 | A | 4/1999 | Eggers et al. | 604/114 |
| 5,891,134 | A | 4/1999 | Goble et al. | 606/27 |
| 5,897,553 | A | 4/1999 | Mulier | 606/41 |
| 5,902,272 | A | 5/1999 | Eggers et al. | 604/114 |
| 5,916,214 | A | 6/1999 | Cosio et al. | 606/41 |
| 5,919,190 | A | 7/1999 | Vandusseldorp | 606/46 |
| 5,921,983 | A | 7/1999 | Shannon, Jr. | 606/45 |
| 5,944,715 | A | 8/1999 | Goble et al. | 606/41 |
| 5,954,716 | A | 9/1999 | Sharkey et al. | 606/32 |
| 5,988,171 | A | 11/1999 | Sohn et al. | 128/848 |
| 6,004,319 | A | 12/1999 | Goble et al. | 606/48 |
| 6,006,755 | A | 12/1999 | Edwards | 128/898 |
| 6,009,877 | A | 1/2000 | Edwards | 128/898 |
| 6,013,076 | A | 1/2000 | Goble et al. | 606/41 |
| 6,015,406 | A | 1/2000 | Goble et al. | 606/41 |
| 6,024,733 | A | 2/2000 | Eggers et al. | 604/500 |
| 6,026,816 | A | 2/2000 | McMillan et al. | 128/898 |
| 6,027,501 | A * | 2/2000 | Goble et al. | 606/41 |
| 6,032,674 | A * | 3/2000 | Eggers et al. | 128/898 |
| 6,039,734 | A | 3/2000 | Goble et al. | 606/41 |
| 6,044,846 | A | 4/2000 | Edwards | 128/898 |
| 6,047,700 | A | 4/2000 | Eggers et al. | 128/898 |
| 6,056,746 | A | 5/2000 | Goble et al. | 606/41 |
| 6,063,079 | A | 5/2000 | Hovda et al. | 606/41 |
| 6,066,134 | A | 5/2000 | Eggers et al. | 606/32 |
| 6,066,139 | A | 5/2000 | Ryan et al. | 606/50 |
| 6,068,628 | A | 5/2000 | Fanton et al. | 606/41 |
| 6,071,281 | A | 6/2000 | Burnside et al. | 606/41 |
| 6,073,052 | A | 6/2000 | Zelickson et al. | 607/100 |
| 6,074,386 | A | 6/2000 | Goble et al. | 606/34 |
| 6,086,585 | A | 7/2000 | Hovda et al. | 606/45 |
| 6,090,106 | A | 7/2000 | Goble et al. | 606/41 |
| 6,093,186 | A | 7/2000 | Goble et al. | 606/34 |
| 6,102,046 | A | 8/2000 | Weinstein et al. | 128/898 |
| 6,105,581 | A | 8/2000 | Eggers et al. | 128/898 |
| 6,109,268 | A | 8/2000 | Thapliyal et al. | 128/898 |
| 6,117,109 | A | 9/2000 | Eggers et al. | 604/114 |
| 6,126,682 | A | 10/2000 | Sharkey et al. | 607/96 |
| 6,142,992 | A | 11/2000 | Cheng et al. | 606/34 |
| 6,149,620 | A | 11/2000 | Baker et al. | 604/22 |
| 6,159,194 | A | 12/2000 | Eggers et al. | 604/500 |
| 6,159,208 | A | 12/2000 | Hovda et al. | 606/41 |
| 6,168,593 | B1 | 1/2001 | Sharkey et al. | 606/34 |
| 6,174,309 | B1 | 1/2001 | Wrublewski et al. | 606/45 |
| 6,179,824 | B1 | 1/2001 | Eggers et al. | 604/500 |
| 6,179,836 | B1 | 1/2001 | Eggers et al. | 606/45 |
| 6,183,469 | B1 | 2/2001 | Thapliyal et al. | 606/41 |
| 6,190,381 | B1 | 2/2001 | Olsen et al. | 606/32 |
| 6,203,542 | B1 | 3/2001 | Ellsberry et al. | 606/41 |
| 6,210,402 | B1 | 4/2001 | Olsen et al. | 606/32 |
| 6,210,405 | B1 | 4/2001 | Goble et al. | 606/41 |
| 6,224,592 | B1 | 5/2001 | Eggers et al. | 606/32 |
| 6,228,078 | B1 | 5/2001 | Eggers | 606/32 |
| 6,228,081 | B1 | 5/2001 | Goble | 606/34 |
| 6,234,178 | B1 | 5/2001 | Goble et al. | 606/32 |
| 6,235,020 | B1 | 5/2001 | Cheng et al. | 606/34 |
| 6,237,604 | B1 | 5/2001 | Burnside et al. | 128/897 |
| 6,238,391 | B1 | 5/2001 | Olsen et al. | 606/41 |
| 6,254,600 | B1 | 7/2001 | Willink et al. | 606/41 |
| 6,258,086 | B1 | 7/2001 | Ashley et al. | 606/41 |
| 6,261,286 | B1 | 7/2001 | Goble et al. | 606/34 |
| 6,261,311 | B1 | 7/2001 | Sharkey et al. | 607/96 |
| 6,264,652 | B1 | 7/2001 | Eggers et al. | 606/41 |
| 6,270,460 | B1 | 8/2001 | McCartan et al. | 600/459 |
| 6,270,476 | B1 | 8/2001 | Santoianni et al. | 604/95.04 |
| 6,277,112 | B1 | 8/2001 | Underwood et al. | 606/32 |
| 6,280,441 | B1 | 8/2001 | Ryan | 606/45 |
| 6,283,961 | B1 | 9/2001 | Underwood et al. | 606/41 |
| 6,293,942 | B1 | 9/2001 | Goble et al. | 606/38 |
| 6,296,636 | B1 | 10/2001 | Cheng et al. | 606/32 |
| 6,296,638 | B1 | 10/2001 | Davison et al. | 606/41 |
| 6,306,134 | B1 | 10/2001 | Goble et al. | 606/42 |
| 6,308,089 | B1 | 10/2001 | von der Ruhr et al. | 600/338 |
| 6,309,387 | B1 | 10/2001 | Eggers et al. | 606/41 |
| 6,312,408 | B1 | 11/2001 | Eggers et al. | 604/114 |
| 6,322,549 | B1 | 11/2001 | Eggers et al. | 604/500 |
| 6,355,032 | B1 | 3/2002 | Hovda et al. | 606/32 |
| 6,363,937 | B1 | 4/2002 | Hovda et al. | 128/898 |
| 6,364,877 | B1 | 4/2002 | Goble et al. | 606/34 |
| 6,379,350 | B1 | 4/2002 | Sharkey et al. | 606/41 |
| 6,379,351 | B1 | 4/2002 | Thapliyal et al. | 606/41 |
| 6,387,093 | B1 | 5/2002 | Ellman et al. | 606/39 |
| 6,391,025 | B1 | 5/2002 | Weinstein et al. | 606/41 |
| 6,411,852 | B1 | 6/2002 | Danek et al. | 607/42 |
| 6,413,254 | B1 | 7/2002 | Hissong et al. | 606/27 |
| 6,416,491 | B1 | 7/2002 | Edwards et al. | 606/41 |
| 6,416,507 | B1 | 7/2002 | Eggers et al. | 606/32 |
| 6,416,508 | B1 | 7/2002 | Eggers et al. | 606/32 |
| 6,416,509 | B1 | 7/2002 | Goble et al. | 606/37 |
| 6,427,089 | B1 | 7/2002 | Knowlton | 607/101 |
| 6,432,103 | B1 | 8/2002 | Ellsberry et al. | 606/41 |
| 6,464,699 | B1 | 10/2002 | Swanson | 606/41 |
| 6,468,274 | B1 | 10/2002 | Alleyne et al. | 606/32 |
| 6,468,275 | B1 | 10/2002 | Wampler et al. | 606/48 |
| 6,482,201 | B1 | 11/2002 | Olsen et al. | 606/41 |
| 6,491,690 | B1 | 12/2002 | Goble et al. | 606/41 |
| 6,517,498 | B1 | 2/2003 | Burbank et al. | 600/564 |
| 6,530,922 | B2 | 3/2003 | Cosman | 606/34 |
| 6,530,924 | B1 | 3/2003 | Ellman et al. | 606/45 |
| 6,551,032 | B1 | 4/2003 | Nolan et al. | 407/13 |
| 6,572,613 | B1 | 6/2003 | Ellman et al. | 606/45 |
| 6,578,579 | B2 | 6/2003 | Burnside | 128/897 |
| 6,589,235 | B2 | 7/2003 | Wong et al. | 606/32 |
| 6,589,237 | B2 | 7/2003 | Woloszko et al. | 606/41 |
| 6,602,248 | B1 | 8/2003 | Sharps et al. | 606/32 |
| 6,620,156 | B1 | 9/2003 | Garito et al. | 606/50 |
| 6,632,193 | B1 | 10/2003 | Davison et al. | 604/22 |
| 6,632,220 | B1 | 10/2003 | Eggers et al. | 606/41 |
| 6,702,810 | B2 | 3/2004 | McClurken et al. | 606/34 |
| 6,736,810 | B2 | 5/2004 | Hoey et al. | 606/34 |
| 6,746,447 | B2 | 6/2004 | Davison et al. | 606/41 |
| 6,749,604 | B1 | 6/2004 | Eggers et al. | 606/41 |
| 6,749,608 | B2 | 6/2004 | Garito et al. | 606/45 |

(56) References Cited

U.S. PATENT DOCUMENTS

| | | | | |
|---|---|---|---|---|
| 6,770,071 | B2 | 8/2004 | Woloszko et al. | 606/41 |
| 6,780,178 | B2 | 8/2004 | Palanker et al. | 600/41 |
| 6,780,180 | B1 | 8/2004 | Goble et al. | 606/41 |
| 6,802,842 | B2 | 10/2004 | Ellman et al. | 606/45 |
| 6,837,887 | B2 | 1/2005 | Woloszko et al. | 606/41 |
| 6,837,888 | B2 | 1/2005 | Ciarrocca et al. | 606/41 |
| 6,896,674 | B1* | 5/2005 | Woloszko et al. | 606/41 |
| 6,920,883 | B2 | 7/2005 | Bessette et al. | 128/898 |
| 6,929,640 | B1 | 8/2005 | Underwood et al. | 606/32 |
| 6,942,662 | B2 | 9/2005 | Goble et al. | 606/48 |
| 6,949,096 | B2 | 9/2005 | Davison et al. | 606/41 |
| 6,955,172 | B2 | 10/2005 | Nelson et al. | 128/848 |
| 6,960,204 | B2 | 11/2005 | Eggers et al. | 606/32 |
| 6,974,453 | B2 | 12/2005 | Woloszko et al. | 606/41 |
| 6,984,231 | B2 | 1/2006 | Goble et al. | 606/37 |
| 6,991,631 | B2 | 1/2006 | Woloszko et al. | 606/41 |
| 7,004,941 | B2 | 2/2006 | Tvinnereim et al. | 606/41 |
| 7,041,102 | B2 | 5/2006 | Truckai et al. | 606/51 |
| 7,066,936 | B2 | 6/2006 | Ryan | 606/45 |
| 7,070,596 | B1 | 7/2006 | Woloszko et al. | 606/41 |
| 7,090,672 | B2 | 8/2006 | Underwood et al. | 606/41 |
| 7,094,215 | B2 | 8/2006 | Davison et al. | 604/22 |
| 7,104,986 | B2 | 9/2006 | Hovda et al. | 606/32 |
| 7,131,969 | B1 | 11/2006 | Hovda et al. | 606/45 |
| 7,160,296 | B2* | 1/2007 | Pearson et al. | 606/42 |
| 7,169,143 | B2 | 1/2007 | Eggers et al. | 606/32 |
| 7,179,255 | B2 | 2/2007 | Lettice et al. | 606/32 |
| 7,186,234 | B2 | 3/2007 | Dahla et al. | 604/22 |
| 7,192,428 | B2 | 3/2007 | Eggers et al. | 606/41 |
| 7,195,630 | B2 | 3/2007 | Ciarrocca | 606/48 |
| 7,201,750 | B1 | 4/2007 | Eggers et al. | 606/41 |
| 7,217,268 | B2 | 5/2007 | Eggers et al. | 606/32 |
| 7,241,293 | B2 | 7/2007 | Davison | 600/410 |
| 7,270,658 | B2 | 9/2007 | Woloszko et al. | 606/32 |
| 7,270,659 | B2 | 9/2007 | Hovda et al. | 606/32 |
| 7,270,661 | B2 | 9/2007 | Dahla et al. | 606/41 |
| 7,276,063 | B2 | 10/2007 | Davison et al. | 606/45 |
| 7,297,143 | B2 | 11/2007 | Woloszko et al. | 606/41 |
| 7,297,145 | B2 | 11/2007 | Ormsby et al. | 606/41 |
| 7,318,823 | B2 | 1/2008 | Sharps et al. | 606/32 |
| 7,331,956 | B2 | 2/2008 | Hovda et al. | 606/32 |
| RE40,156 | E | 3/2008 | Sharps et al. | 606/32 |
| 7,357,798 | B2 | 4/2008 | Sharps et al. | 606/32 |
| 7,387,625 | B2 | 6/2008 | Hovda et al. | 606/32 |
| 7,419,488 | B2 | 9/2008 | Ciarrocca et al. | 606/41 |
| 7,429,260 | B2 | 9/2008 | Underwood et al. | 606/32 |
| 7,429,262 | B2 | 9/2008 | Woloszko et al. | 606/46 |
| 7,435,247 | B2 | 10/2008 | Woloszko et al. | 604/45 |
| 7,442,191 | B2 | 10/2008 | Hovda et al. | 606/41 |
| 7,445,618 | B2 | 11/2008 | Eggers et al. | 604/48 |
| 7,449,021 | B2 | 11/2008 | Underwood et al. | 606/32 |
| 7,462,178 | B2 | 12/2008 | Woloszko et al. | 607/105 |
| 7,468,059 | B2 | 12/2008 | Eggers et al. | 606/32 |
| 7,491,200 | B2 | 2/2009 | Underwood et al. | 606/32 |
| 7,507,236 | B2 | 3/2009 | Eggers et al. | 606/41 |
| 7,572,251 | B1 | 8/2009 | Davison et al. | 604/500 |
| 7,632,267 | B2 | 12/2009 | Dahla | 606/41 |
| 7,691,101 | B2 | 4/2010 | Davison et al. | 606/41 |
| 7,704,249 | B2 | 4/2010 | Woloszko et al. | 606/48 |
| 7,708,733 | B2 | 5/2010 | Sanders et al. | 606/41 |
| 7,824,398 | B2 | 11/2010 | Woloszko et al. | 606/45 |
| 7,879,034 | B2 | 2/2011 | Woloszko et al. | 606/48 |
| 2002/0029036 | A1 | 3/2002 | Goble et al. | 606/38 |
| 2002/0049438 | A1 | 4/2002 | Sharkey et al. | 606/41 |
| 2003/0013986 | A1 | 1/2003 | Saadat | 600/549 |
| 2003/0014050 | A1 | 1/2003 | Sharkey et al. | 606/45 |
| 2003/0088245 | A1 | 5/2003 | Woloszko et al. | 606/41 |
| 2003/0158545 | A1 | 8/2003 | Hovda et al. | 606/32 |
| 2003/0171743 | A1 | 9/2003 | Tasto et al. | 606/32 |
| 2003/0208196 | A1 | 11/2003 | Stone | 606/41 |
| 2003/0212396 | A1 | 11/2003 | Eggers et al. | 606/41 |
| 2004/0116922 | A1 | 6/2004 | Hovda et al. | 606/41 |
| 2004/0127893 | A1 | 7/2004 | Hovda | 606/41 |
| 2004/0230190 | A1 | 11/2004 | Dahla et al. | 604/41 |
| 2005/0004634 | A1 | 1/2005 | Hovda et al. | 606/41 |
| 2005/0043728 | A1 | 2/2005 | Ciarrocca | 606/48 |
| 2005/0261754 | A1 | 11/2005 | Woloszko et al. | 606/32 |
| 2005/0283149 | A1 | 12/2005 | Thorne et al. | 606/48 |
| 2005/0288665 | A1 | 12/2005 | Woloszko et al. | 606/41 |
| 2006/0036237 | A1 | 2/2006 | Davison et al. | 606/41 |
| 2006/0095031 | A1 | 5/2006 | Ormsby | 606/34 |
| 2006/0178670 | A1 | 8/2006 | Woloszko et al. | 606/48 |
| 2006/0189971 | A1 | 8/2006 | Eggers et al. | 606/32 |
| 2006/0253117 | A1 | 11/2006 | Hovda et al. | 128/898 |
| 2006/0259025 | A1 | 11/2006 | Dahla | 607/108 |
| 2007/0106288 | A1 | 5/2007 | Woloszko et al. | 606/41 |
| 2007/0149966 | A1 | 6/2007 | Dahla et al. | 606/41 |
| 2007/0161981 | A1 | 7/2007 | Sanders et al. | 606/41 |
| 2007/0208335 | A1 | 9/2007 | Woloszko et al. | 606/41 |
| 2007/0282323 | A1 | 12/2007 | Woloszko et al. | 606/41 |
| 2008/0200972 | A1* | 8/2008 | Rittman et al. | 607/117 |
| 2010/0204690 | A1 | 8/2010 | Bigley et al. | 606/41 |
| 2012/0101494 | A1 | 4/2012 | Cadouri et al. | 606/41 |
| 2012/0203219 | A1 | 8/2012 | Evans et al. | 606/33 |
| 2012/0226273 | A1 | 9/2012 | Nguyen et al. | 606/41 |
| 2013/0066317 | A1 | 3/2013 | Evans et al. | 606/48 |
| 2013/0197506 | A1 | 8/2013 | Evans et al. | 606/48 |

FOREIGN PATENT DOCUMENTS

| | | | | |
|---|---|---|---|---|
| EP | 0703461 | A2 | 3/1996 | G01B 27/02 |
| EP | 0740926 | A1 | 11/1996 | A61B 17/39 |
| EP | 0754437 | A2 | 1/1997 | A61B 17/39 |
| EP | 0694290 | B1 | 11/2000 | A61B 18/04 |
| EP | 2198799 | | 6/2010 | A61B 18/14 |
| FR | 2313949 | | 1/1977 | A61N 3/02 |
| GB | 2 308 979 | | 7/1997 | A61B 17/36 |
| GB | 2 308 980 | | 7/1997 | A61B 17/36 |
| GB | 2 308 981 | | 7/1997 | A61B 17/36 |
| GB | 2 327 350 | | 1/1999 | A61B 17/39 |
| GB | 2 327 351 | | 1/1999 | A61B 17/39 |
| GB | 2 327 352 | | 1/1999 | A61B 17/39 |
| GB | 2479582 | | 10/2011 | A61B 18/14 |
| JP | 57-57802 | | 4/1982 | A61B 1/00 |
| JP | 57-117843 | | 7/1982 | A61B 17/39 |
| JP | 58-13213 | | 1/1983 | A61B 18/12 |
| JP | 10-43198 | | 2/1998 | A61B 17/42 |
| WO | 90/03152 | | 4/1990 | A61B 17/39 |
| WO | 90/07303 | | 7/1990 | A61B 17/39 |
| WO | 92/21278 | | 12/1992 | A61B 5/04 |
| WO | 93/13816 | | 7/1993 | A61B 17/36 |
| WO | 93/20747 | | 10/1993 | A61B 5/00 |
| WO | 94/04220 | | 3/1994 | |
| WO | 94/08654 | | 4/1994 | A61M 37/00 |
| WO | 94/10924 | | 5/1994 | A61B 17/39 |
| WO | 94/26228 | | 11/1994 | A61G 17/36 |
| WO | 95/34259 | | 12/1995 | A61F 5/48 |
| WO | 96/00042 | | 1/1996 | A61B 17/39 |
| WO | 96/23449 | | 8/1996 | A61B 17/39 |
| WO | 96/37156 | | 11/1996 | A61B 17/00 |
| WO | 96/39914 | | 12/1996 | A61B 1/00 |
| WO | 97/00646 | | 1/1997 | A61B 17/39 |
| WO | 97/00647 | | 1/1997 | A61B 17/39 |
| WO | 97/15237 | | 5/1997 | A61B 18/12 |
| WO | 97/18765 | | 5/1997 | A61B 17/36 |
| WO | 97/24073 | | 7/1997 | A61B 17/39 |
| WO | 97/24074 | | 7/1997 | A61B 17/39 |
| WO | 97/24993 | | 7/1997 | A61B 17/39 |
| WO | 97/24994 | | 7/1997 | A61B 17/39 |
| WO | 97/30644 | | 8/1997 | A61B 17/39 |
| WO | 97/30645 | | 8/1997 | A61B 17/39 |
| WO | 97/30646 | | 8/1997 | A61B 17/39 |
| WO | 97/30647 | | 8/1997 | A61B 17/39 |
| WO | 97/41785 | | 11/1997 | A61B 17/39 |
| WO | 97/41786 | | 11/1997 | A61B 17/39 |
| WO | 97/41787 | | 11/1997 | A61B 17/39 |
| WO | 97/41788 | | 11/1997 | A61B 17/39 |
| WO | 97/43969 | | 11/1997 | A61B 17/39 |
| WO | 97/43970 | | 11/1997 | A61B 17/39 |
| WO | 97/43972 | | 11/1997 | A61B 17/39 |
| WO | 97/43973 | | 11/1997 | A61B 17/39 |
| WO | 97/44092 | | 11/1997 | A61B 17/39 |
| WO | 97/48345 | | 12/1997 | A61B 17/39 |
| WO | 97/48346 | | 12/1997 | A61B 17/39 |

(56) References Cited

FOREIGN PATENT DOCUMENTS

| WO | 98/03117 | 1/1998 | ............ A61B 17/00 |
|---|---|---|---|
| WO | 98/07468 | 2/1998 | ............ A61N 1/40 |
| WO | 98/27879 | 7/1998 | ............ A61B 17/36 |
| WO | 98/27880 | 7/1998 | ............ A61B 17/39 |
| WO | 99/08613 | 2/1999 | ............ A61B 17/39 |
| WO | 99/09919 | 3/1999 | ............ A61B 18/12 |
| WO | 99/17690 | 4/1999 | ............ A61F 7/12 |
| WO | 99/30655 | 6/1999 | ............ A61F 7/12 |
| WO | 99/51155 | 10/1999 | ............ A61B 17/36 |
| WO | 99/51158 | 10/1999 | ............ A61B 17/39 |
| WO | 00/62698 | 10/2000 | ............ A61B 18/14 |
| WO | 01/87154 | 5/2001 | ............ A61B 5/05 |
| WO | 02/36028 | 5/2002 | ............ A61B 18/12 |
| WO | 02/085230 | 10/2002 | ............ A61B 18/14 |
| WO | 03/005882 | 1/2003 | ............ A61B 18/14 |
| WO | 03/024305 | 3/2003 | |
| WO | 03/047446 | 6/2003 | ............ A61B 18/12 |
| WO | 03/068095 | 8/2003 | ............ A61B 18/14 |
| WO | 2004/050171 | 6/2004 | |
| WO | 2005/125287 | 12/2005 | ............ A61B 18/00 |
| WO | 2006/002337 | 1/2006 | ............ A61B 18/14 |
| WO | 2006/125007 | 11/2006 | ............ A61B 18/14 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, Bet al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John a., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atheroscherotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.

(56) References Cited

OTHER PUBLICATIONS

Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, Clinica, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Rand et al., "Effect of Elecctrocautery on Fresh Human Articular Cartilage", J. Arthro. Surg., vol. 1, pp. 242-246, 1985.
European Search Report for EP00123324.6 4 pgs, Mailed Jan. 16, 2001.
European Search Report for EP00928246 4 pgs, Mailed Mar. 7, 2008.
European Search Report for EP09153983 9 pgs, Mailed Apr. 1, 2009.
European Search Report for EP98964730.0 3 pgs, Mailed Nov. 20, 2000.
European Search Report for EP99922855.4 3 pgs, Aug. 2, 2001.
European Search Report for EP05762588 3 pgs, Apr. 12, 2010.
European Search Report for EP06760025.4 5 pgs, Nov. 10, 2010.
PCT International Preliminary Examination Report for PCT/US00/10674 4pgs, Mailed Mar. 7, 2001.
PCT International Preliminary Examination Report for PCT/US98/26624 4pgs, Mailed Oct. 12, 1999.
PCT International Preliminary Examination Report for PCT/US99/10062 3 pgs, Jun. 20, 2000.
PCT International Preliminary Report on Patentability for PCT/US05/22373 4pgs, Dec. 28, 2006.
PCT International Preliminary Report on Patentability for PCT/US06/19095 6pgs, Nov. 20, 2007.
PCT International Search Report for PCT/US00/10674 1 pg, Mailed Jul. 27, 2000.
PCT International Search Report for PCT/US03/38782 1 pg, Mailed Jun. 30, 2004.
PCT International Search Report for PCT/US05/22373 1 pg, Mailed Oct. 3, 2006.
PCT International Search Report for PCT/US06/19095 2 pgs Mailed Oct. 4, 2007.
PCT International Search Report for PCT/US96/08077 1 pg, Mailed Sep. 16, 1996.
PCT International Search Report for PCT/US98/26624 1 pg, Mailed Mar. 3, 1999.
PCT International Search Report for PCT/US99/10062 1 pg, Mailed Aug. 23, 1999.
UK Search Report for GB1111622.5 4pgs, Oct. 26, 2011.
UK Search Report for GB1202275.2 7pgs, May 11, 2012.

\* cited by examiner

SYSTEMS AND METHODS FOR TURBINATE REDUCTION

FIELD OF THE INVENTION

The present invention relates generally to the field of electrosurgery, and more particularly to surgical systems and methods which employ high frequency electrical energy to reduce and treat target tissues, such as tissues within the nasal area. The present invention is particularly suited for turbinate reduction surgery; a treatment for excessive nasal drainage or difficulty breathing.

BACKGROUND

Sinuses are the air-filled cavities insides the facial bones that open into the nasal cavities. Sinusitis is the inflammation of the mucous membranes of one or more of the paranasal sinus cavities. Sinusitis is often associated with a viral or bacterial upper respiratory infection that spreads to the sinuses. When the sinus opening becomes blocked, the cavities fill, producing deep pain and pressure. Postnasal or nasal drainage, nasal congestion with pressure, headaches, sinus infections and nasal polyps are most commonly associated with chronic sinusitis.

Treatment of mild sinusitis typically involves antibiotics, decongestants and analgesics, and is designed to prevent further complications. For more severe or chronic sinusitis, surgery is often necessary to return the nose and sinuses to normal function, particularly with patients who have undergone years of allergy treatment and still suffer from sinus blockage, or patients born with small sinuses and nasal passages. Recent developments in the field of endoscopic surgical techniques and medical devices have provided skilled physicians with instrumentation and methods to perform complicated paranasal sinus surgical procedures. Improved visualization of the nasal cavity and the paranasal sinuses, for example, has now made these anatomical areas more accessible to the endoscopic surgeon. As a result, functional endoscopic sinus surgery (FESS) has become the technique of choice in the surgical approach to sinus disease.

Another nasal symptom, runny noses (e.g., allergic rhinitis or vasomotor rhinitis), is typically caused by small shelf-like structures in the nose called turbinates. Turbinates are responsible for warming and humidifying the air passing through the nose into the lungs. When the air contains an irritant, the turbinates react to the airborne particles by swelling and pouring mucus, as if the body were trying to block and cleanse the breathing passage. For temporary relief of swollen turbinates, decongestant nasal sprays and pills are often prescribed. These measures, however, have limited effectiveness, and the long term use of such nasal sprays typically makes the problem worse. Moreover, decongestant pills may cause high blood pressure, increase the heart rate and, for some people, cause sleeplessness.

In the past several years, powered instrumentation, such as microdebrider devices and lasers, has been used to remove polyps or other swollen tissue in functional endoscopic sinus surgery. Microdebriders are disposable motorized cutters having a rotating shaft with a serrated distal tip for cutting and resecting tissue. The handle of the microdebrider is typically hollow, and it accommodates a small vacuum, which serves to aspirate debris. In this procedure, the distal tip of the shaft is endoscopically delivered through a nasal passage into the sinus cavity of a patient, and an endoscope is similarly delivered through the same or the opposite nasal passage to view the surgical site. An external motor rotates the shaft and the serrated tip, allowing the tip to cut the polyps or other tissue responsible for the sinus blockage. Once the critical blockage is cleared, aeration and drainage are reestablished and the sinuses heal and return to their normal function.

While microdebriders have been promising, these devices suffer from a number of disadvantages. For one thing, the tissue in the nasal and sinus cavities is extremely vascular, and the microdebrider severs blood vessels within this tissue, usually causing profuse bleeding that obstructs the surgeon's view of the target site. Controlling this bleeding can be difficult since the vacuuming action tends to promote hemorrhaging from blood vessels disrupted during the procedure. In addition, the microdebrider often must be removed from the nose periodically to cauterize severed blood vessels, which lengthens the procedure. Moreover, the serrated edges and other fine crevices of the microdebrider can easily become clogged with debris, which requires the surgeon to remove and clean the microdebrider during the surgery, further increasing the length of the procedure. More serious concerns, however, are that the microdebrider is not precise, and it is often difficult, during the procedure, to differentiate between the target sinus tissue, and other structures within the nose, such as cartilage, bone or cranial. Thus, the surgeon must be extremely careful to minimize damage to the cartilage and bone within the nose, and to avoid damaging nerves, such as the optic nerve.

Lasers were initially considered ideal for sinus surgery because lasers ablate or vaporize tissue with heat, which also acts to cauterize and seal the small blood vessels in the tissue. Unfortunately, lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to judge how deeply the laser is cutting. Because healthy tissue, cartilage, bone and/or cranial nerves often lie within close proximity of the sinus tissue, it is essential to maintain a minimum depth of tissue damage, which cannot always be ensured with a laser.

Treatments involving RF electrical energy based devices have previously been described, wherein the electrodes are predominantly disposed at the instrument tip, and are therefore limited in active size due to the small diameter of instrument required to access nasal passages. Such methods and apparatus are more fully described in previously filed applications, U.S. Pat. Nos. 6,053,172; 6,063,079; 6,659,106 and 7,442,191, the full disclosures of which have been incorporated by reference.

SUMMARY

The present disclosure presents an improved electrosurgical apparatus for treating tissue at a target site. The apparatus includes a shaft with a proximal end and a distal end portion and an active electrode and return electrode disposed on the distal end portion of the shaft. The apparatus also has a plurality of apertures though the return electrode, operable to deliver an electrically conductive fluid to the shaft distal end portion.

In yet another aspect an electrosurgical apparatus is disclosed for removing tissue from a body structure including a shaft having a proximal end, a distal end portion and a distal tip, the distal end portion having at least one active electrode and a return electrode, wherein the return electrode encircles at least a portion of the shaft and extends distally and proximally from the active electrode.

In yet another aspect an electrosurgical system is disclosed for treating tissue of a body structure. The system includes an instrument and a high frequency voltage supply. The instrument includes a shaft with a proximal end, a distal end portion and a distal tip, with at least one active electrode and a return electrode disposed on the distal end portion of said shaft. The return electrode may encircle the shaft and extend distally and proximally from the at least one active electrode and a plurality of apertures though the return electrode operable to deliver fluid to the shaft distal end portion. The return electrode and active electrode are electrically connected to the voltage supply.

In yet another aspect a method of performing a medical procedure on a body is disclosed. The method includes positioning an instrument distal end portion lateral to the target site. The distal end portion includes at least one active electrode and a return electrode, electrically connected to a high frequency voltage supply. The return electrode has a plurality of fluid delivery apertures through the return electrode. Electrically conductive fluid is then delivered through the fluid delivery apertures, so as to wet the return electrode and allow a current path to flow between the active electrode and the return electrode. High frequency voltage is then supplied between the at least one active electrode and return electrode, this high frequency voltage being sufficient to treat at least a portion of the target tissue. During the step of supplying, the instrument distal end portion may be axially rotated so as to form a bore hole within the target tissue.

The present disclosure includes a number of important technical advantages. One technical advantage is that the lateral position of the electrodes allows for a relatively larger electrode for a minimal diameter instrument distal portion; the electrodes are not limited to the instrument diameter size compared with an instrument design with the electrodes limited to the tip only. This may make the instrument and system easier and quicker to use, as the treatment surface may then be relatively large, compared to instruments with the electrodes limited to the instrument tip. An additional technical advantage is the position of the lateral fluid delivery apertures, which allows for significant fluid delivery spread out over a broad surface area. This may optimize the return electrode "wetted" surface area by allowing for a more evenly and uniformly coated surface, creating a more uniform and even tissue effect. An additional advantage is that the size of the wetted return surface area is not as limited compared with designs that locate the return on the instrument tip, allowing for a larger treatment surface and larger, more optimum surface area ratios, between the active electrode and return. Another advantage is that the return may encircle the active electrode without adding significantly to the instrument diameter, compared with instruments with the electrodes limited to the instrument tip. Encircling the active electrode may improve the uniformity of the tissue effect. An additional advantage is that the suction apertures are less limited in size or number. There may be more suction apertures than a design that limits the suction apertures to the instrument tip, creating better aspiration and improving the surgeon's ability to see the surgical site. Additional advantages will be apparent to those of skill in the art and from the figures, description and claims provided herein.

BRIEF DESCRIPTION OF THE DRAWINGS

The invention may best be understood by reference to the following description taken in conjunction with the accompanying drawings in which.

DETAILED DESCRIPTION

Figure 1:
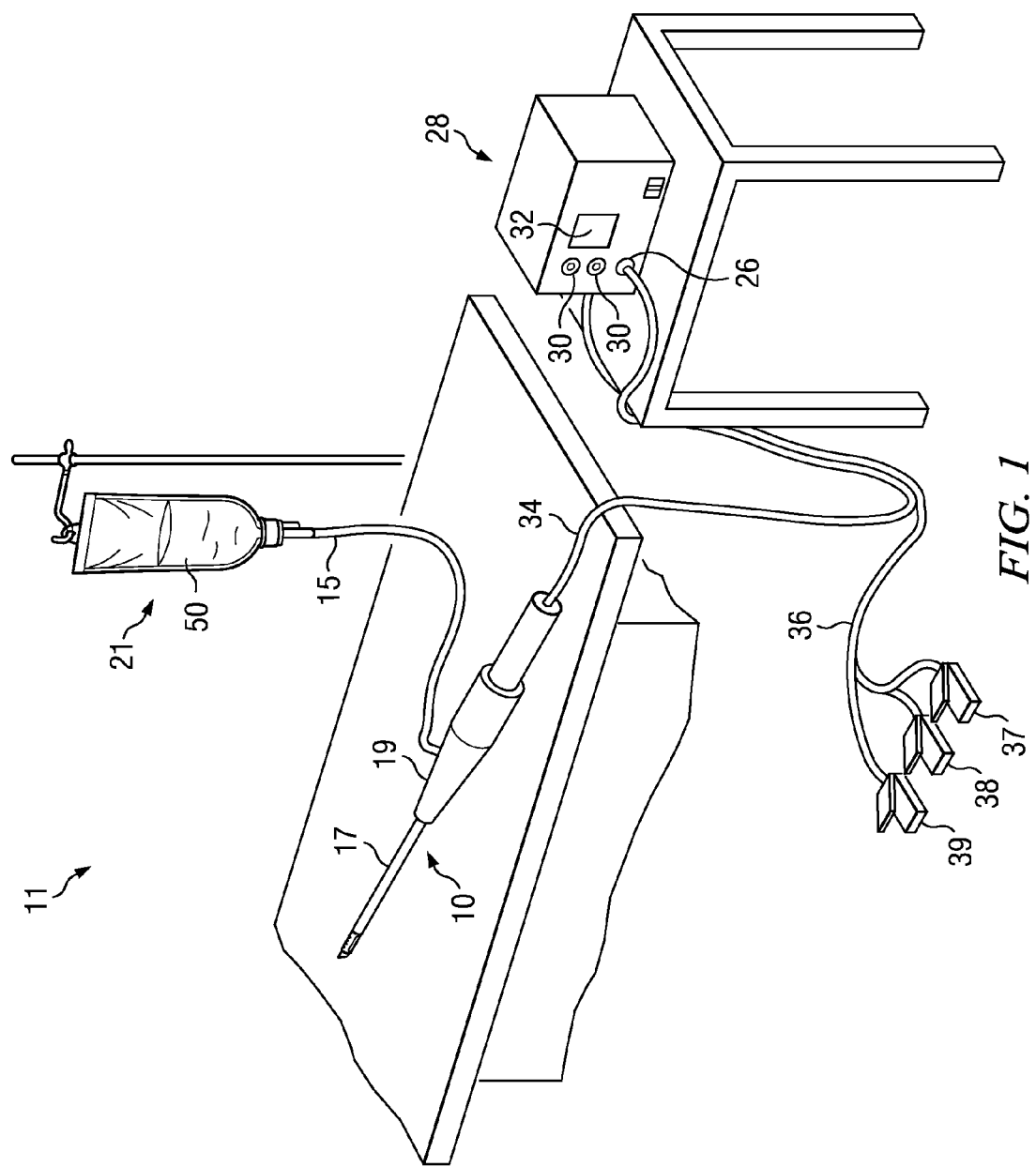
FIG. 1 shows a perspective view of an electrosurgical system according to at least certain embodiments.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The treatment device of the present invention may have a variety of configurations as described above. However, one variation of the invention employs a treatment device using Coblation® technology.

As stated above, the assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882, the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomenon can be found in commonly assigned U.S. Pat. Nos. 6,355,032; 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

In one example of a Coblation® device for use with the present invention, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation® treatment device for use in the present invention may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency.

Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Referring to FIG. 1, an exemplary electrosurgical system 11 for treatment of tissue in accordance with the present disclosure will now be described in detail. Electrosurgical system 11 generally comprises electrosurgical handpiece, instrument, apparatus or probe 10 connected to an electrosurgical controller (i.e., power supply) 28 for providing high frequency voltage to a target site; and a fluid source 21 for supplying electrically conducting fluid 50 to probe 10 via fluid delivery tube 15. In addition, electrosurgical system 11 may include an endoscope (not shown) with a fiber optic head light for viewing the surgical site, particularly in sinus procedures or procedures in the ear or the back of the mouth. The endoscope may be integral with probe 10, or it may be part of a separate instrument. The system 11 may also include a vacuum source (not shown) for coupling to a suction or aspiration lumen or tube (not shown) in the probe 10 for aspirating the target site.

Exemplary electrosurgical probe 10 comprises a handle 19 and an elongate shaft 17 extending from handle 19. The proximal and distal portions of handle 19 typically comprise a plastic material that is easily molded into a suitable shape for handling by the surgeon. As shown, a connecting cable 34 has a connector 26 for electrically coupling the active electrode and return electrode (described in more detail in later figures) on probe 10 to power supply 28. Power supply 28 has an operator controllable voltage level adjustment 30 to change the applied voltage level, which is observable at a voltage level display 32. Power supply 28 may also include first, second and third foot pedals 37, 38, 39 and a cable 36 which is removably coupled to power supply 28. The foot pedals 37, 38, 39 allow the surgeon to remotely adjust the energy level applied to active electrode 58. In an exemplary embodiment, first foot pedal 37 is used to place the power supply into the "ablation" mode and second foot pedal 38 places power supply 28 into a "subablation" mode (i.e., contraction, coagulation or other types of tissue modification without volumetric tissue removal). The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" modes voltage level adjustment 30 or third foot pedal 39 may be used to adjust the voltage level to adjust the degree or aggressiveness of the ablation.

Of course, it will be recognized that the voltage and modality of the power supply may be controlled by other input devices, by a variety of switches or toggles placed on the handle 19 for example. However, applicant has found that foot pedals are convenient methods of controlling the power supply while manipulating the probe during a surgical procedure.

In the subablation mode, the power supply 28 applies a low enough voltage to the active electrode to avoid vaporization of the electrically conductive fluid and subsequent molecular dissociation of the tissue. The surgeon may automatically toggle the power supply between the ablation and subablation modes by alternatively stepping on foot pedals 37, 38, respectively. This allows, for example, the surgeon to quickly move between coagulation and ablation in situ, without having to remove his/her concentration from the surgical field or without having to request an assistant to switch the power supply. By way of example, as the surgeon sculpts soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37.

Figure 2A:
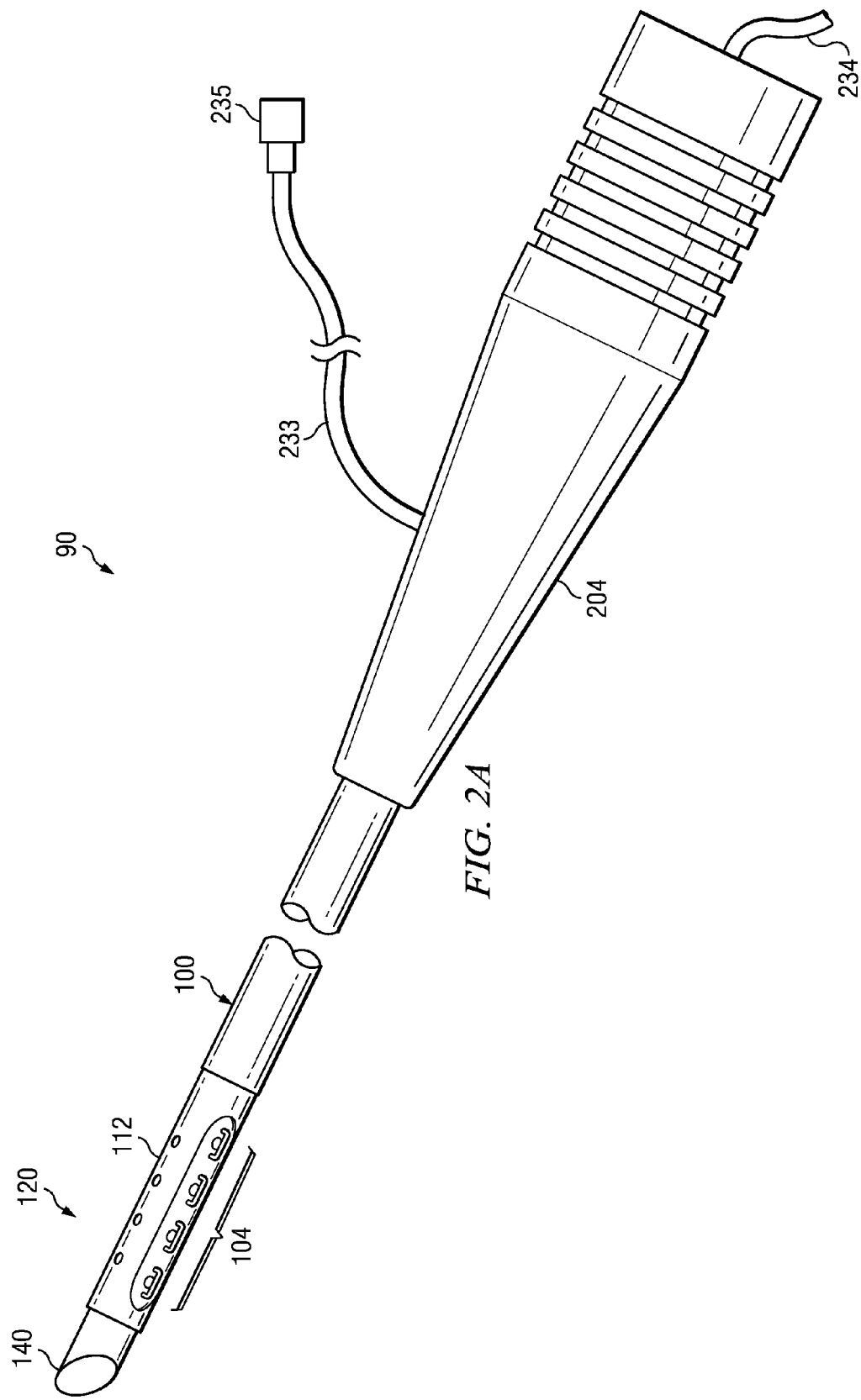
FIG. 2A shows an apparatus for treating tissue according to at least certain embodiments.

FIG. 2A illustrates an exemplary electrosurgical instrument 90 constructed according to the principles of the present disclosure. As shown in FIG. 2A, probe 90 generally includes an elongate shaft 100 which may be flexible or rigid, and a handle 204 coupled to the proximal end of shaft 100. Shaft 100 may include a bend or curve (not shown) that may allow the distal portion 120 of shaft 100 to be offset or at a different angle from the shaft proximal section and handle 204. This offset may facilitate procedures that require an endoscope, because the endoscope can, for example, be introduced through the same nasal passage as the shaft 100 without interference between handle 204 and the eyepiece of the endoscope. In alternative embodiments, shaft 100 may be malleable so that the surgeon may create the curve or bend that is preferred for the specific patient or endoscopic needs.

Handle 204 typically comprises a plastic material that is easily molded into a suitable shape for handling by the surgeon. Handle 204 defines an inner cavity (not shown) that houses the electrical connections (not shown) and provides a suitable interface for connection to an electrical connecting cable 234. As shown in FIG. 2A, a fluid tube or inlet 233 extends through an opening in handle 204, and may include a connector 235 for connection to a fluid supply source, for supplying electrically conductive fluid to the instrument distal portion 120 and subsequently to the target site. Depending on the configuration of the distal surface of shaft 100, fluid tube 233 may extend through a single lumen (not shown) within shaft 100, or the shaft 100 may be a hollow lumen for providing a conduit for fluid (described in more detail later), or tube 233 may be coupled to a plurality of lumens (not shown) that extend through or along shaft 100. In alternative embodiments, fluid tube 233 may extend along the exterior of shaft 100 to a point just proximal of distal portion 120. Probe 90 may also include a valve or equivalent structure (not shown) located on the instrument 90 or tubing 233, for controlling the flow rate of the electrically conducting fluid to the target site.

In certain embodiments, the distal portion of shaft 100 comprises a flexible material which may be deflected relative to the longitudinal axis of the shaft 100. Such deflection may be selectively induced by mechanical tension of a pull wire, for example, or by a shape memory wire that expands or contracts by externally applied temperature changes. A bend in the distal portion of shaft 100 is particularly advantageous in the treatment of sinus tissue as it allows the surgeon to reach the target tissue within the nose as the shaft 100 extends through the nasal passage. Of course, it will be recognized that the shaft may have different angles depending on the procedure. For example, a shaft having a 90° bend angle may be particularly useful for accessing tissue located in the back portion of the mouth and a shaft having a 10° to 30° bend angle may be useful for accessing tissue near or in the front portion of the mouth or nose.

In the embodiment shown in FIG. 2A, probe 90 generally includes a shaft distal portion 120 and distal tip 140. Distal tip 140 may not be energized but may include a sharp, jagged or piercing edge or tip, operable to help gain access, dissect tissue or create a window into tissue such as a polyp or turbinate. Distal tip 140 may be rigid, enabling it to be more readily directed into a targeted body structure and preferably access the inside of the body structure. In this embodiment, distal tip 140 may be manufactured from a ceramic or electrically insulating material or non-organic material. In alternate embodiments, distal tip 140 may be manufactured from an electrically conducting material and selectively energized so as to gain easier access to tissues or provide hemostasis or a desired tissue effect at the instrument distal tip 140 as needed.

Distal portion 120 includes at least one return electrode 112 and at least one active electrode 104. As shown in more detail in FIG. 2B, return electrode 112 encircles at least a portion of the shaft distal portion 120 and may extend distally and proximally relative to the active electrode 104 so that the active electrode 104 is generally surrounded. Return electrode 112 may be approximately tubular shaped and extend along shaft 100. Return electrode 112 is shown with an opening, channel or slot, so as to encircle the active electrode 104 and said opening is configured so that there is a substantially uniform gap or dimension 106 between the closest point on the active electrode 104 to the adjacent return electrode opening edge 114. Alternative embodiments may include multiple openings or slots with active electrodes disposed therein. By maintaining a substantially consistent distance along a significant portion of the length of the opening edge, this return electrode 112 configuration is believed to maintain a more uniform tissue effect along the instrument distal portion 120. In addition, the smaller dimension 106 is, the lower the energy or voltage may be required by a power supply to create a required tissue effect, and the more localized the tissue effect may be, creating a very controlled tissue effect, which is preferable to the surgeon. This may minimize unwanted tissue treatment outside the intended area. In the embodiment shown, dimension 106 may be between approximately 0.2 mm and 3 mm.

Figure 2B:
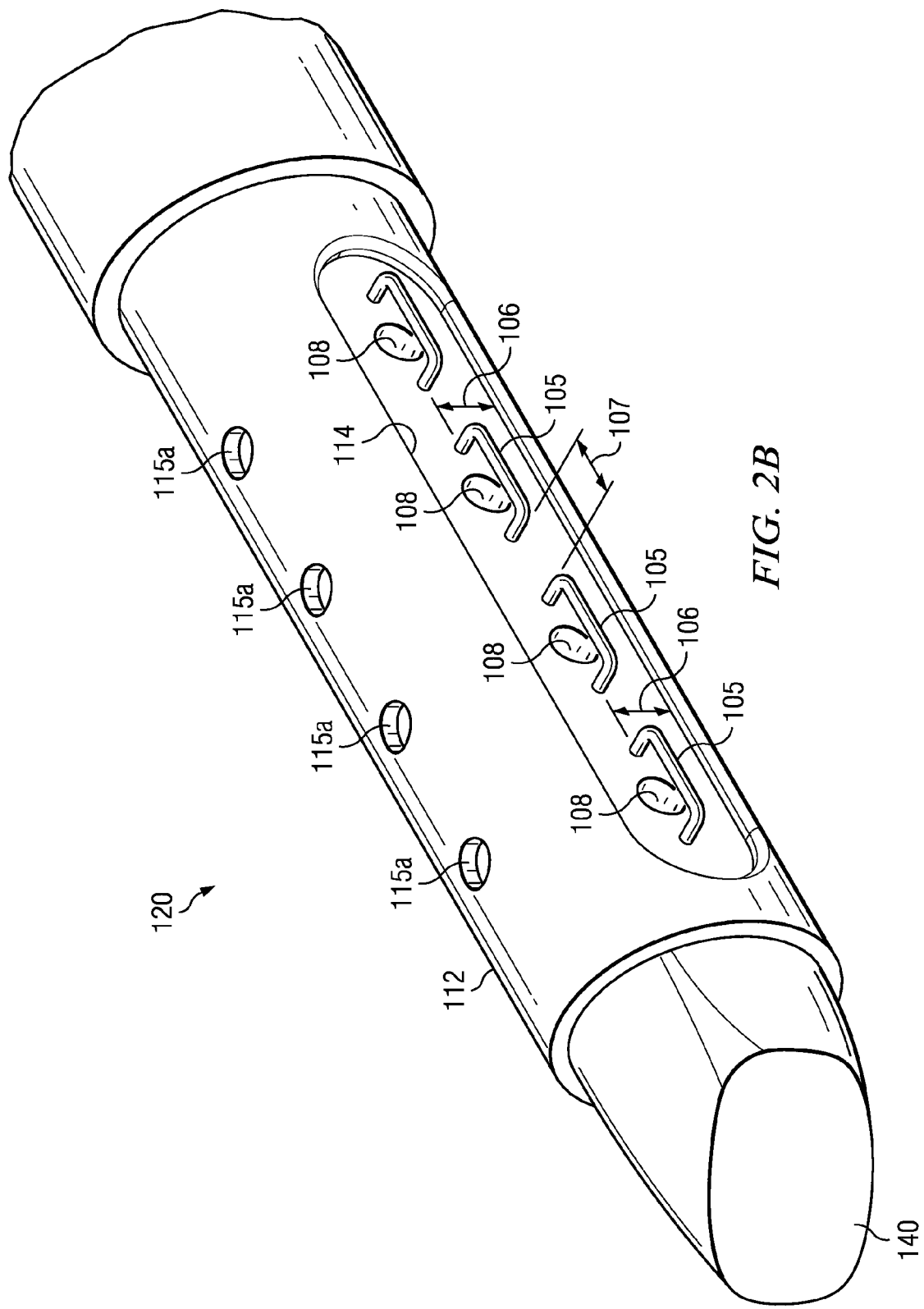
FIG. 2B shows an instrument shaft distal end portion, according to at least certain embodiments.
Figure 2C:
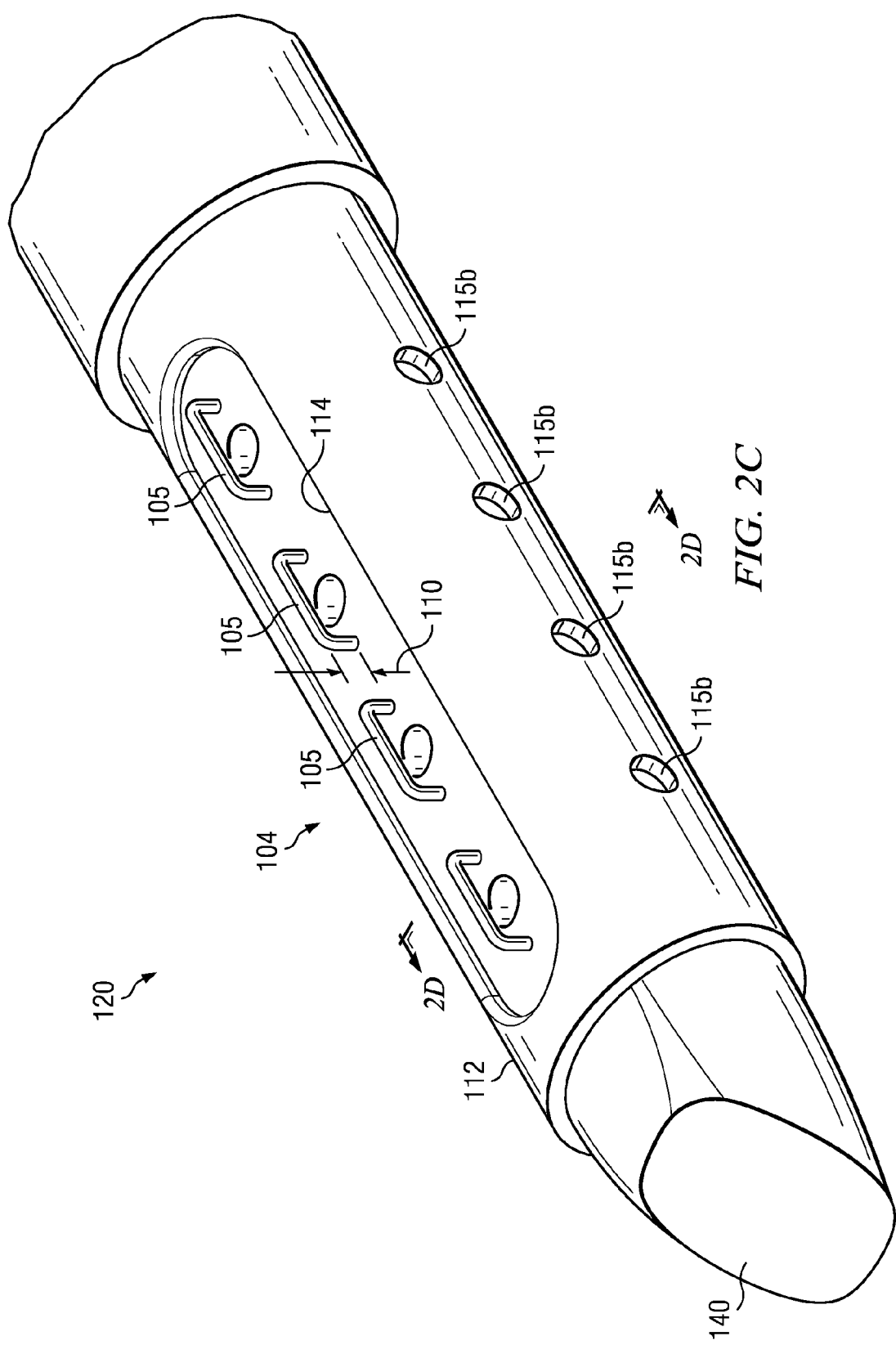
FIG. 2C shows an instrument shaft distal end portion, according to at least certain embodiments.

Return electrode 112 is not directly connected to active electrode 104. To complete this current path so that an electrical current may flow between active electrode 104 and return electrode 112, electrically conducting fluid (e.g., isotonic saline) is caused to flow there between. In order to supply fluid, return electrode 112 includes at least one discharge aperture 115a formed through the return electrode 112. This at least one aperture 115a is oriented in a generally radial direction with respect to shaft 100. In the shown embodiment, multiple apertures 115a span approximately a distance corresponding to the length of the active electrode 104, in a row of axially spaced apertures 115a, and there may be a plurality of aperture rows on either side of the active electrode 104, shown as 115a in FIG. 2B and 115b shown in FIG. 2C. These apertures 115a and 115b are operable to deliver an electrically conductive fluid supply to the external surface of the return electrode 112, so as to create an electrical current path from the active electrode 104 and form a net wetted return electrode area. Apertures 115a, 115b are connected to a fluid supply element as described in later figures, and are operable to transfer fluid from this fluid supply element to the return electrode external surface.

The number, size, shape and location of apertures 115a and 115b, as well as the rate of fluid supply determine how much of the return is "wetted" and how uniform the wetted area is. Apertures may be a variety of shapes such as ovals, elongate slits or circles. Alternative embodiments may comprise one elongate slit that may vary in width along its length so as to keep a uniform fluid delivery along the distal portion length. The goal of apertures 115a, 115b is to minimize areas on the return electrode 112 surface that are dry. It is preferable for the return electrode surface to be uniformly wetted to create a more-even electrical field between the active electrode 104 and return electrode 112, so as to create a more reliable and uniform tissue effect. Areas of the return external surface that are relatively dry may induce resistive heating effects and unwanted tissue effect is those areas.

In general, the ratio between the wetted return electrode area and active electrode surface area should be between 2:1 and 10:1, and more optimally around 8:1. Electrode surface area may be defined as the exposed conductive surface of the active electrodes 104. As will be apparent to those of skill in the art, the active electrode surface area depends on the size of the active electrode itself Additionally, in certain embodiments all surface areas may be further altered or adjusted using coatings or electrical insulation so as to control any active electrode surface area value.

In order to minimize areas of high currently density on the return electrode 112, and create any unwanted tissue effect, return electrode edges 114 as well as any other edges such as those around the apertures 115a, 115b, may preferably be smooth, with minimal burrs or sharp point and preferably would have an edge radius (not shown) of at least 0.005 inches.

Active electrode 104 is disposed on the lateral side of shaft distal portion 120, and may comprise an elongate row or array of staple shaped electrically conductive protrusions 105, extending radially from the shaft distal portion 120. Electrode gap 107 between each staple end may preferably be minimal so as to decrease any dead space or areas with little or sub-optimal tissue effect. Electrode gap 107 is preferably between 0.2 and 2 mm. Probe 90 may predominantly be rotated during tissue treatment and too large a gap 107 may necessitate more rotations, repeated back and forth rotations or a corkscrew motion or axially translational motion more so than an axially rotational motion. This may make the instrument use more difficult and sub-optimal. Each staple 105 may be electrically coupled to each other, with only one connection to a voltage supply. One electrical connection to a voltage supply may make wiring of the instrument simpler. Alternatively each staple 105 may be connected individually to a voltage supply, so as to be controlled individually.

Return electrode 112 is shown with edges 114 to form an approximate oval shape encircling active electrode 104. In alternative embodiments, return electrode 112 may encircle each individual staple electrode 105 in the form of alternative shapes, such as multiple circles. Alternatively, the return electrode 112 may encircle the active electrode 104 with a varying elongate form, such as multiple hour glass shapes, to more closely approximately an equal distance or more even dimension 106 around the active electrode 104.

Staple 105 may have a height or extension 110 sufficient to engage and treat target tissue. Portions of staple 105 may be coated or insulated, so as to control the active electrode surface area and maintain the preferred surface area ratios. For example, the staple legs or underside may be coated.

Adjacent each staple 105 there may be an aspiration aperture 108. Aspiration aperture 108 may be connected to a vacuum or suction element (described in more detail later), and aspiration aperture 108 may be operable to aspirate any excess fluid, gases or tissue from the target area. This may improve target site visibility. Staple 105 configurations may provide at least two functions while the instrument 90 is in use. Staple 105 provides the desired tissue effects to target tissue, as well as further reducing or morsellating any large pieces of tissue before aspirating tissue. Larger tissue pieces may clog up any aspiration lumen or aperture reducing suction power, and therefore an optimal staple 105 configuration may prevent these larger pieces of tissue from accessing the suction aperture 108, by providing a physical barrier as well as by further morsellating the larger tissue pieces before they enter any aspiration aperture 108. In one embodiment, staple height 110 may be approximately between and including 0.015 and 0.035 inches, and more preferably of 0.030 inches, so as to properly engage mucosal tissue such as turbinates as well as minimize suction lumen clogging.

Figure 2D:
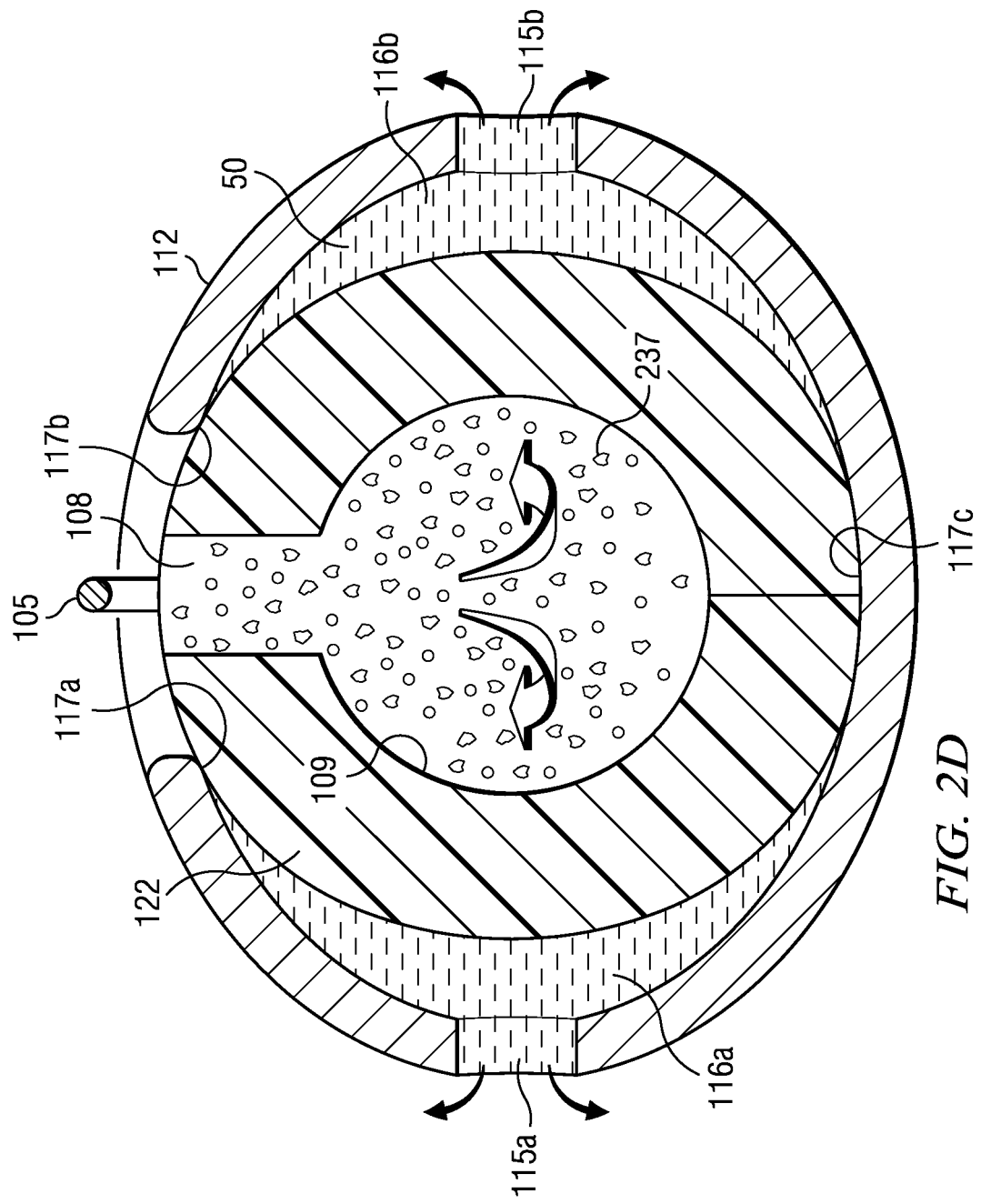
FIG. 2D shows a perpendicular cross section view of an instrument distal end portion according to at least certain embodiments.

Looking now at FIG. 2D, a cross section of one embodiment of a shaft distal end portion 120 is shown, including the staple electrode 105, aspiration aperture 108 and return electrode 112. Staple electrode 105 is shown here to have a circular cross section. However, alternative embodiments could include rectangular, square or alternative shapes with edges and flats to create a more focused or defined tissue effect in certain areas. In general, active electrodes 104 with edges may create focused or preferential electrical fields at any corners or edges by way of high current density generation, and may be used to direct or create a preference in tissue effect. Additionally, alternate cross sections may provide a structural integrity to the electrodes as it pushes against tissue. The cross section may also vary along the electrode length.

Aspiration aperture 108 is fluidly connected with aspiration lumen 109, and is operable to transport fluid, tissue fragments, and gases 237 from the ablative process away from the target site, as shown by the arrows in the figure. Lumen 109 may be formed by a tubular electrode insulator 122. Alternatively, there may be a separate tube or tubes fluidly connected with each aspiration aperture 108. Electrode insulator 122 may form aspiration lumen 109 at the distal end portion only and connect to other lumens or tubes proximal of the shaft distal end portion 120. Lumen or tubes (not shown) may extend within shaft 100 for a portion of shaft length, or lumens may exit shaft proximal to shaft distal portion 120. Alternatively, electrode insulator may extend along most of the shaft length and connect to an outlet or suction source (neither shown) within instrument handle 204.

FIG. 2D also shows fluid supply lumens 116a and 116b, formed in an annular space between the outer wall of insulator 122 and inner surfaces of return electrode 112, together with contact points 117a, 117b and 117c, creating at least two annular gaps between insulator 122 and return electrode 112. Lumens 116a, 116b are operable to supply electrically conductive fluid 50 to apertures 115a and 115b, and are also operable to restrict fluid 50 from being directly, fluidly connected with staple electrode 105, without first traversing the outer surface of return electrode 112 to create a wetted area discussed earlier. Return electrode 112 is shown formed in an approximate oval shape to as to create lumens 116a, 116b, with contact points 117a, 117b and contact surface 117c. Alternative embodiments may include a more circular formed return electrode 112 with the use of a sealant, epoxy, spacer, a lobed lumen or custom o-rings in appropriate areas adjacent to contact points 117a, 117b, to prevent fluid 50 from leaching out directly to the staple electrode 105.

Figure 2E:
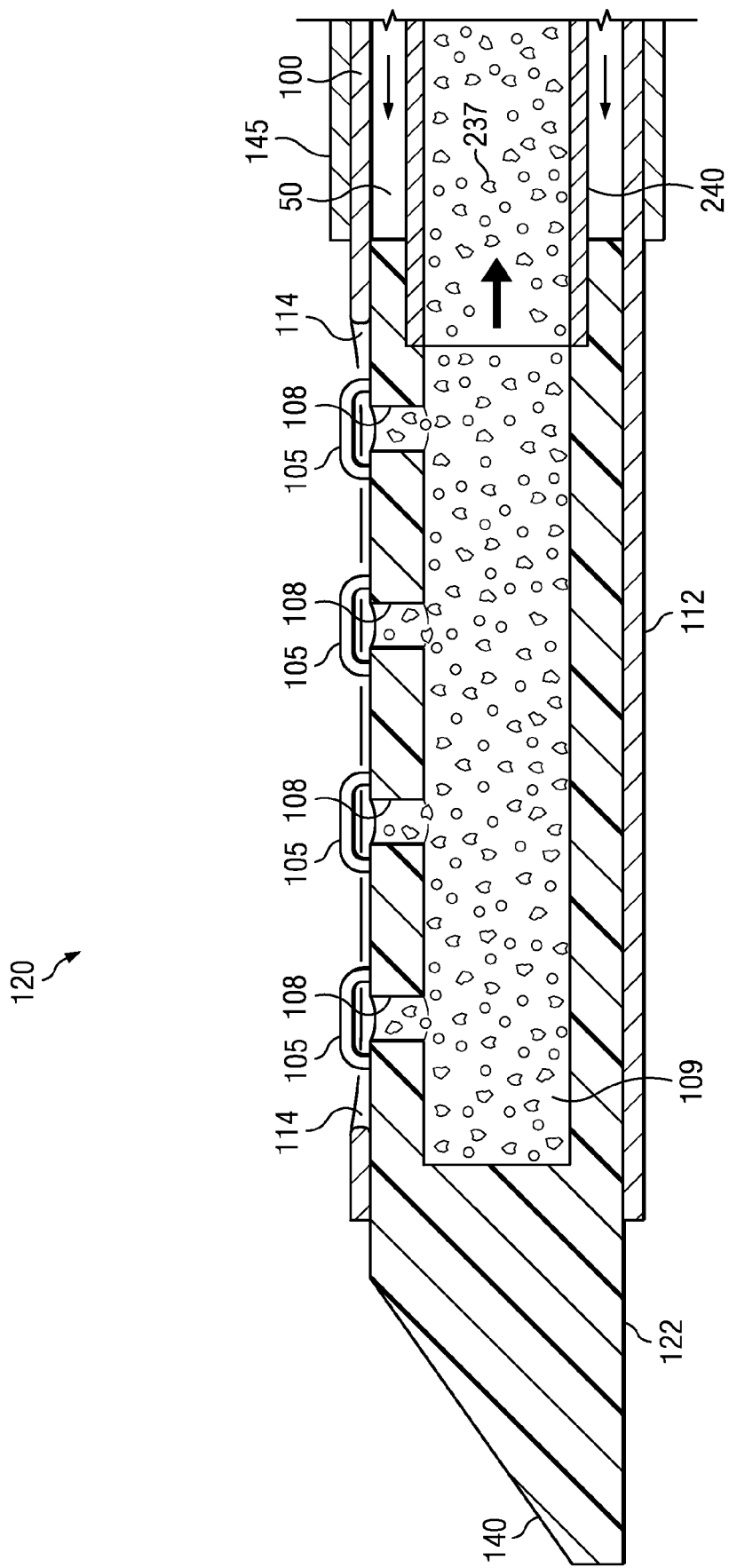
FIG. 2E shows a longitudinal cross section view of an instrument distal end portion according to at least certain embodiments.

FIG. 2E shows an exemplary longitudinal cross sectional view of shaft distal end portion 120, including aspiration apertures 108, staple electrodes 105 and return electrode 112. Return electrode 112 has smooth and preferably rounded edges 114 to minimize high current density formation and any corresponding unwanted tissue effect adjacent the return electrode 112. Instrument shaft 100 may comprise a hollow, electrically conductive shaft, so as to form the return electrode at the distal end portion 120, and so as to be operable to connect a power supply with the return electrode 112. An insulating layer 145 may then be disposed proximal the distal end portion 120 to form return electrode 112 and insulate electrical energy along the remains of the shaft 100. Insulating layer 145 may comprise shrink tubing, coatings or adhesive. Alternative embodiments may comprise a shaft 100 comprising an insulative material with the conductive return electrode connected at the distal end portion only with electrical connections between a power supply and the return electrode 112 made via alternative methods such as wires or traces.

Electrode staples 105 are electrically connected to a power supply such as one described in FIG. 1. Staples 105 may be electrically connected to each other using wires or cables for example, which is not shown in the figure. Staples 105 may also be formed as one elongate component that is later overmolded or coated to create the preferred exposed areas. Alternatively, each staple 105 may be individually connected to a power supply using electrically connecting means such as tracing, wires or conducting ribbons routed from each respective staple. Any electrically connecting means may then route from active electrode 104 along shaft 100, internally or externally to connect to a power supply.

Electrically conductive fluid 50 may be supplied via a fluid delivery element, comprising a lumen formed by hollow shaft 100 (see fluid delivery flow arrows) up until shaft distal portion 120, wherein delivery element may further include lumens 116a, 116b (not shown here) formed by an annular gap between return electrode 112 and tubular insulator 122. Lumens 116a, 116b may then fluidly connect with apertures 115a, 115b (described earlier and not shown here). In alternative embodiments, the fluid delivery element may comprise a fluid tube extending along an outer surface of the shaft 100, the tube having an inlet to lumens 116a, 116b positioned proximal to the return electrode 112. In further alternative embodiments, fluid path may include fluid tubes (not shown) extending within shaft 100.

Disposed within shaft 100 there may be a fluid aspiration tube 240, operable to transport fluids, gases and tissue particulate 237 away from surgical site via apertures 108 and lumen 109. Tube 240 is fluidly connected with lumen 109 and may extend proximally along the shaft to handle 204. Alternatively, tube may exit shaft 100 at a place along the shaft and be disposed outside the shaft to the suction source (not shown).

Insulator 122 may also extend distally and form distal tip 140. Insulator 122 may be an inorganic material such as a ceramic, or any material capable of insulating the active electrode 104 from the return electrode 112 during application of electrical energy. Insulator 122 also may mechanically provide electrode support and a dissecting function at the distal tip 140, which is generally operable to create windows or access to target sites with a body structure, as will be described later.

Figure 2F:
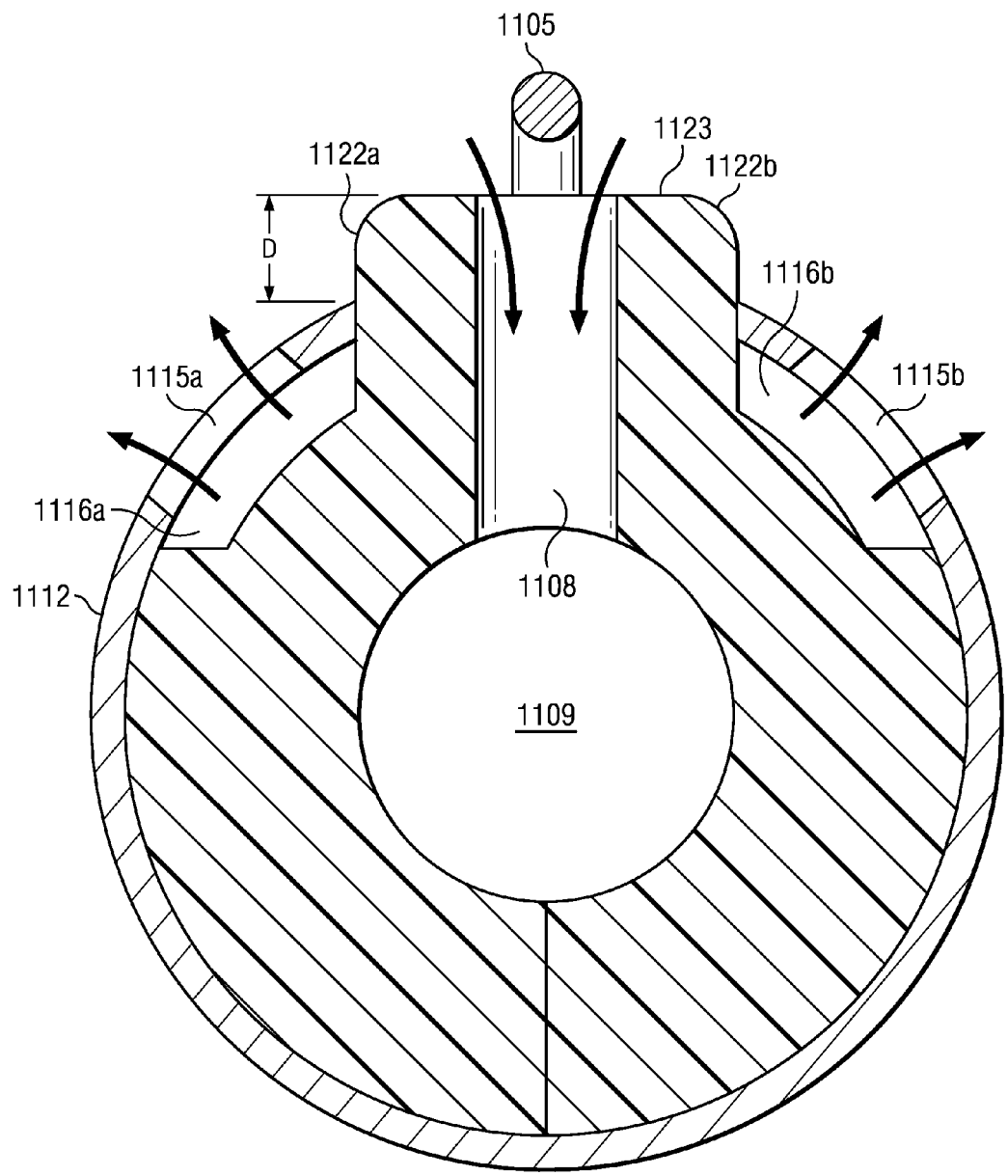
FIG. 2F shows a perpendicular cross section view of an instrument distal end portion according to at least certain embodiments.

Referring now to FIG. 2F, a cross section of an additional embodiment of a shaft distal end portion 1120 is shown, including staple electrode 1105, aspiration aperture 1108 and return electrode 1112. Aspiration aperture 1108 is fluidly connected with aspiration lumen 1109, wherein lumen 1109 is formed by a tubular electrode insulator 1122a, 1122b. Electrode insulator 1122a, 1122b is comprised of two complimentary pieces that are joined symmetrically along the longitudinal axis of the device and as assembled are oriented in a manner that may be familiarly described as a "clam shell" orientation. Electrode insulator 1122a, 1122b is characterized by a cut-out section on its surface forming fluid supply lumens 1116a, 1116b in the annular space between the outer wall of insulator 1122a, 1122b and return electrode 1112. Fluid supply lumens 1116a, 1116b may be disposed at an acute angle relative to the longitudinal axis of the device. Lumens 1116a, 1116b are fluidly connected to discharge apertures 1115a, 1115b disposed through return electrode 1112 such that conductive fluid is supplied to staple electrodes 1105 by traversing over the outer surface of return electrode 1112 to create a wetted area as discussed above. Electrode insulator 1122a, 1122b may also have a working surface 1123 for supporting staple electrode 1105 that forms a standoff distance that extends a distance D from return electrode 1112. By providing a standoff distance D from return electrode 1112 to working surface 1123, a substantially constant gap distance between staple electrode 1105 and return electrode 1112 is formed, which is believed to maintain a more uniform tissue effect along the instrument distal portion 1120. In certain embodiments, standoff distance D is between and includes 0.010 inches and 0.025 inches.

Figure 2G:
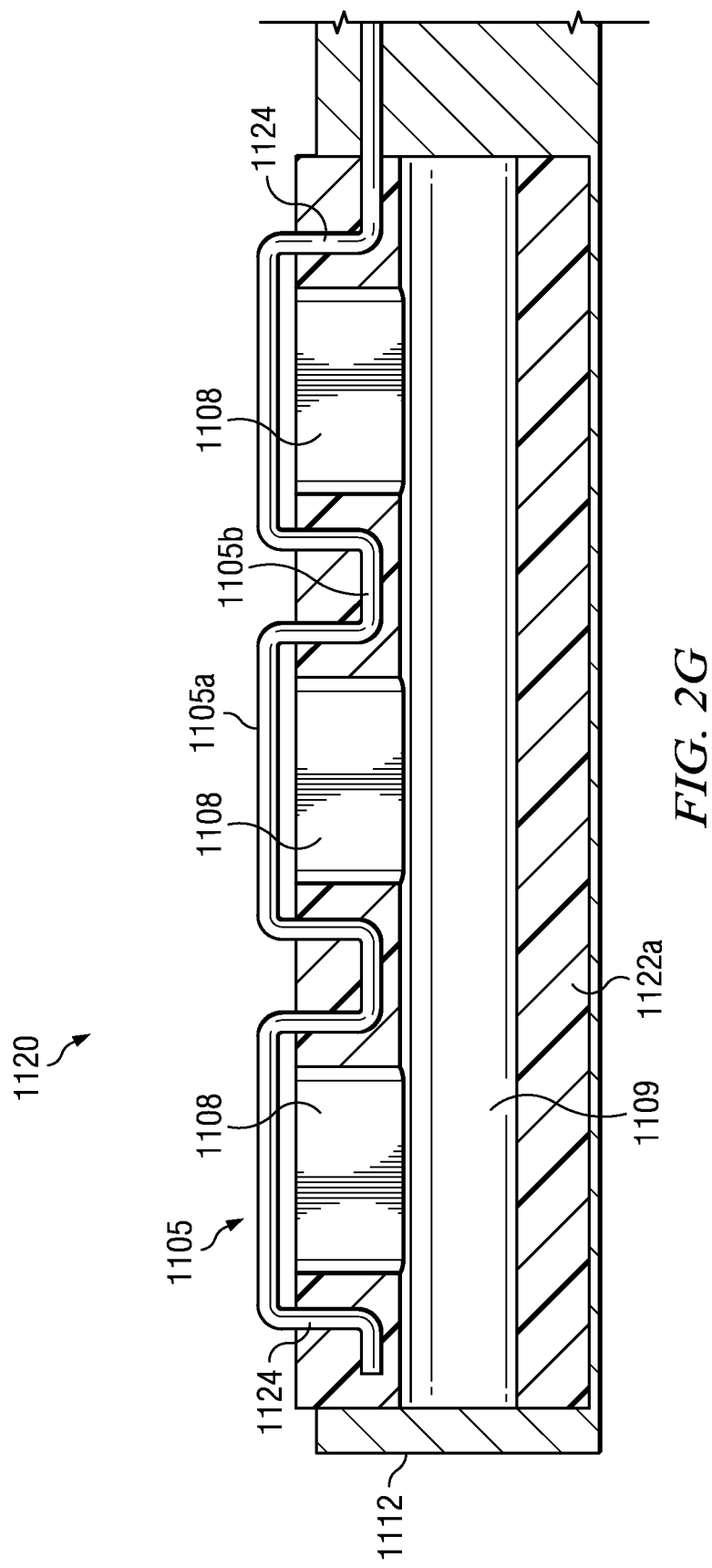
FIG. 2G shows a longitudinal cross section view of an instrument distal end portion according to at least certain embodiments.

FIG. 2G illustrates a longitudinal cross sectional view of shaft distal end portion 1120 according to at least some embodiments. Electrode insulator 1122a defines aspiration apertures 1108 which are fluidly connected to aspiration lumen 1109. Return electrode 1112 encircles electrode insulator 1122a and has smooth, preferably rounded edges to minimize high current density formation and any corresponding unwanted tissue effect adjacent the return electrode 1112. Staple electrodes 1105 are formed as one elongate member in the present embodiment, with portions 1105a of the electrode exposed and portions 1105b of the electrode disposed within channels 1124 formed in electrode insulator 1122a. Staple electrodes 1105 are electrically connected to a power supply such as one described in FIG. 1.

Figure 3A:
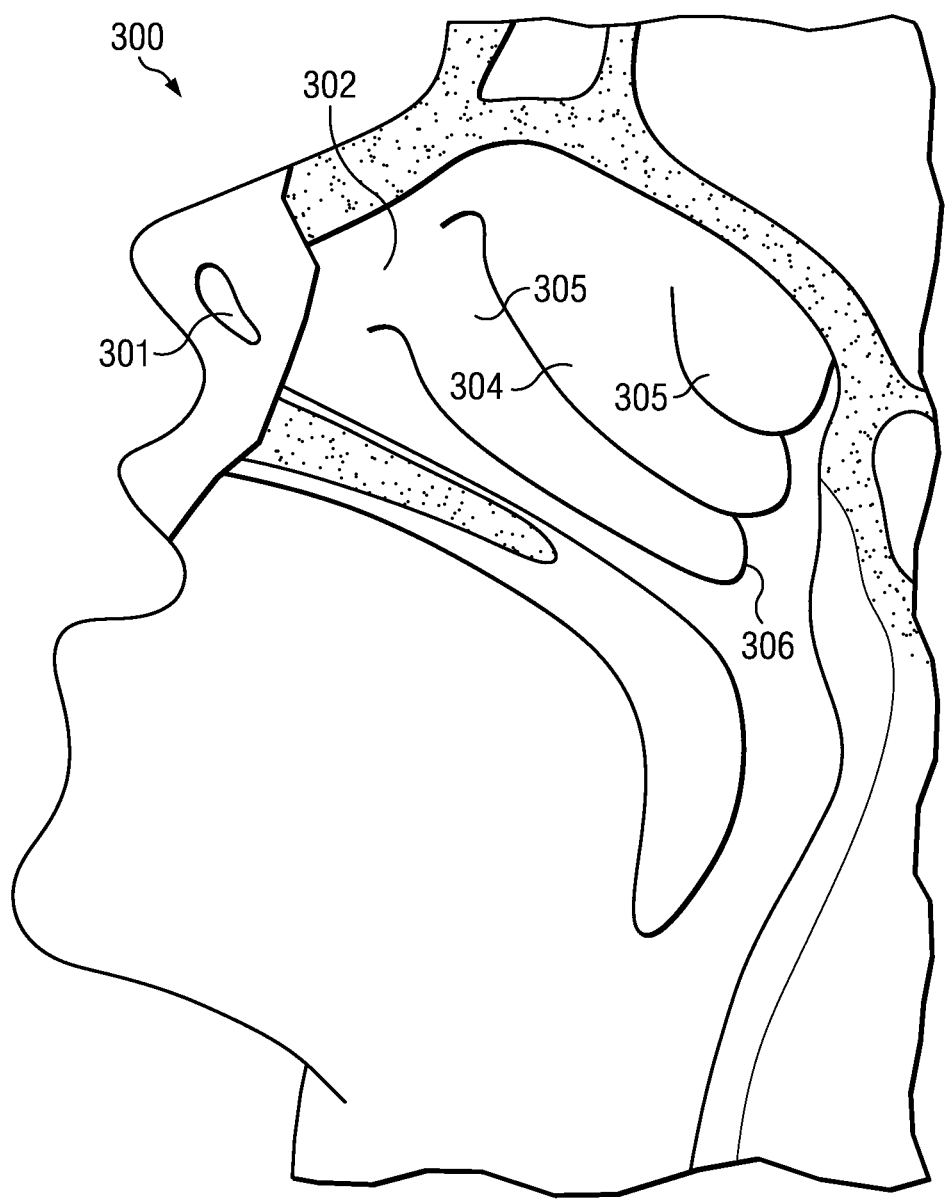
FIG. 3A shows a nasal cavity for potential treatment using an electrosurgical system constructed according to at least certain embodiments.

FIG. 3A illustrates a nasal cavity, being prepared for treatment for enlarged body structures, such as polyps or turbinates, according to the present invention. In these procedures, the polyps, turbinates or other sinus tissue may be ablated or reduced (e.g., by tissue contraction) to clear the blockage and/or prevent further swelling of the turbinates to reestablish normal sinus function. For example, in chronic rhinitis, which is a collective term for chronic irritation or inflammation of the nasal mucosa with hypertrophy of the nasal mucosa, the inferior turbinate may be reduced by ablation or contraction. Alternatively, a turbinectomy or mucotomy may be performed by removing a strip of tissue from the lower edge of the inferior turbinate to reduce the volume of the turbinate. For treating nasal polypi, which comprises benign pedicled or sessile masses of nasal or sinus mucosa caused by inflammation, the nasal polypi may be contracted or shrunk, or ablated by the method of the present invention. For treating severe sinusitis, a frontal sinus operation may be performed to introduce the electrosurgical probe to the site of blockage. The present invention may also be used to treat diseases of the septum, e.g., ablating or resecting portions of the septum for removal, straightening or reimplantation of the septum.

The present invention is particularly useful in reducing enlarged turbinates by volumetrically removing a portion of the turbinates. As shown in FIG. 3A, a patient's nose 300 comprises a nasal cavity 302 having a set of turbinates 305, including a middle nasal concha 304 and an inferior nasal concha 306. The inferior nasal concha 306 generally comprises an anterior portion and a posterior portion. It has been found that treating the inferior nasal concha 306, typically the anterior portion, does not substantially degrade its function. According to the present disclosure, the distal end of probe 90 may be introduced through nasal passage 301 into the nasal cavity 302.

Figure 3B:
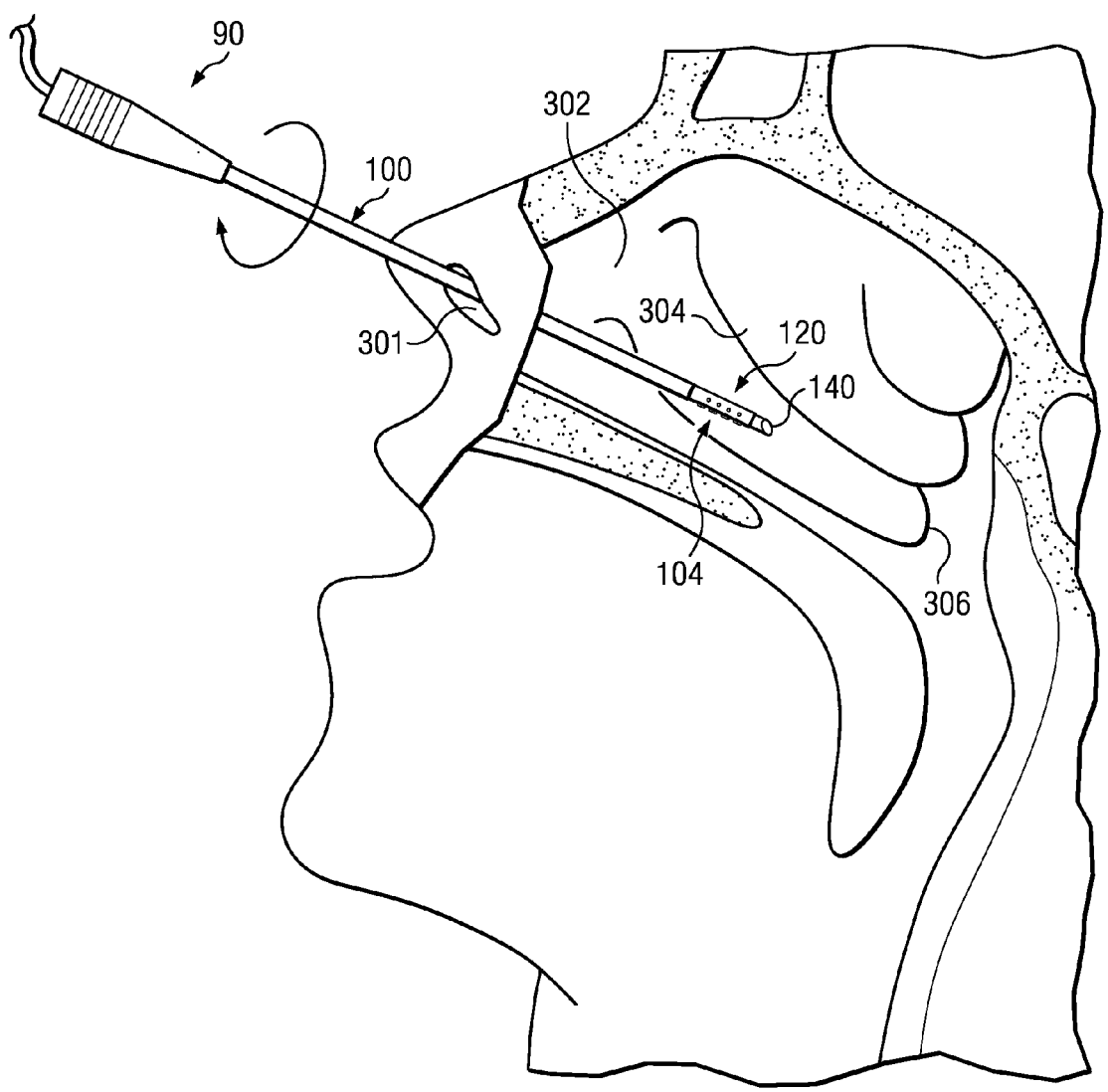
FIG. 3B shows a nasal cavity with an electrosurgical instrument disposed within, the instrument shown according to at least certain embodiments.

FIG. 3B illustrates an exemplary endoscopic sinus surgery according to the teachings in the present disclosure. An endoscope may first be introduced (not shown) through one of the nasal passages 301 to allow the surgeon to view the target site, e.g., the sinus cavities. Shaft 100 may have a bend or curve to facilitate use of both the endoscope and the probe 90 in the same nasal passage (i.e., the handles of the two instruments do not interfere with each other in this embodiment). Alternatively, the endoscope may be introduced transorally through the inferior soft palate to view the nasopharynx. Suitable nasal endoscopes for use with the present invention are described in U.S. Pat. Nos. 4,517,962; 4,844,052; 4,881,523 and 5,167,220, the complete disclosures of which are incorporated herein by reference for all purposes.

Alternatively, the endoscope may include a sheath having an inner lumen for receiving the electrosurgical probe shaft 100. In this embodiment, the shaft 100 will extend through the inner lumen to a distal opening in the endoscope. The shaft will include suitable proximal controls for manipulation of its distal end during the surgical procedure.

As shown in FIG. 3B, the probe distal portion 120 is introduced through nasal passage 301 into the nasal cavity 302. Depending on the location of the blockage, the distal tip 140 will be positioned adjacent the blockage in the nasal cavity 302, or in one of the paranasal sinuses 304, 306. Once the surgeon has reached the point of major blockage, surgeon may chose to use distal tip 140 to access blocked area through blunt or sharp dissection. Alternatively, the surgeon may chose to use an alternate instrument to make a window to gain access to sinus tissue. Once access has been gained, electrically conductive fluid may be delivered. The fluid flows over the return electrode 112 to wet the return electrode surface at the distal end portion of the shaft. The rate of fluid flow may be controlled with a valve (not shown) such that the zone between the tissue and electrode support 122 is constantly immersed or coated with the fluid and the return electrode 112 is sufficiently wetted. The power supply 28 (shown in FIG. 1) is then turned on and adjusted such that a high frequency voltage difference is applied between active electrode 104 and return electrode 112. The electrically conductive fluid provides the conduction path (see current flux lines in FIG. 3C) between active electrode 104 and the return electrode 112. Apparatus 90 may then be rotated to bore out or core out sinus tissue to reduce or debulk tissue mass.

Figure 3C:
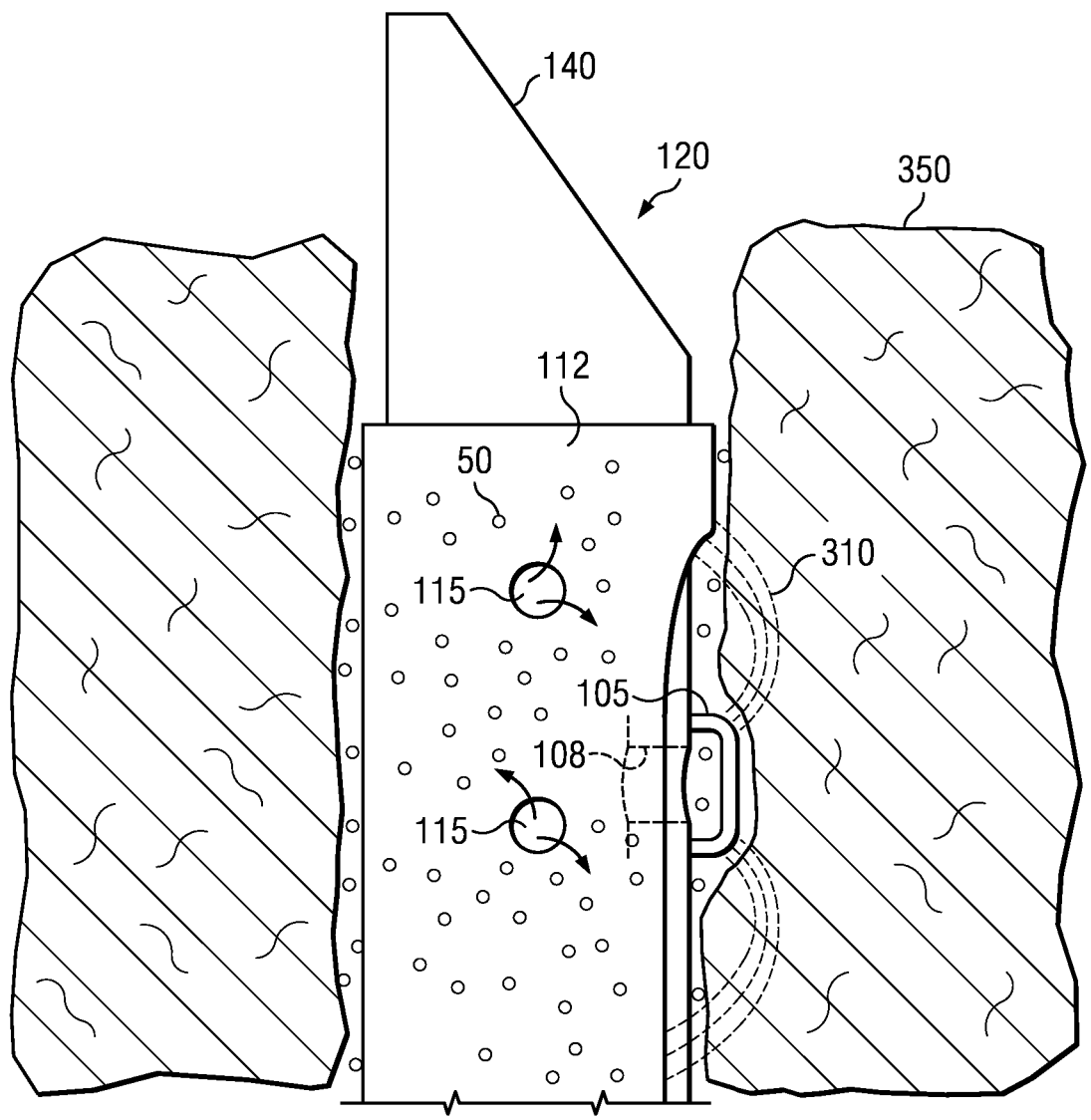
FIG. 3C shows an instrument shaft distal end portion according to at least certain embodiments, disposed adjacent target tissue.

FIG. 3C illustrates the removal of target tissue in more detail. Apparatus distal end portion 120 and distal tip 140 are shown, similar to an embodiment described in FIG. 2, shown within target tissue 350 such as sinus or turbinate tissue. As shown, a high frequency voltage difference may be applied between staple electrode 105 and return electrode 112 such that electric current 310 flows through conductive fluid 50 and tissue 350. Conductive fluid 50 is supplied though apertures 115 to wet return electrode 112. High frequency voltage may be sufficient to convert the electrically conductive fluid (not shown) between the target tissue 350 and staple electrode 105 into an ionized vapor layer or plasma. As a result of the applied voltage difference between staple electrode 105 and the target tissue 350 (i.e., the voltage gradient across the plasma layer), charged particles 615 in the plasma (viz., electrons) are accelerated towards the tissue.

During the process, gases may be aspirated through aspiration apertures 108 fluidly coupled to a vacuum source. In addition, excess electrically conductive fluid 50, and other fluids (e.g., blood) may be aspirated from the target site to facilitate the surgeon's view. During ablation of the tissue, the residual heat generated by the current flux lines 310 (typically less than 150° C.), will usually be sufficient to coagulate any severed blood vessels at the site. If not, the surgeon may switch a power supply into a coagulation mode by lowering the voltage to a level below the threshold for fluid vaporization, as discussed above. This simultaneous hemostasis results in less bleeding and facilitates the surgeon's ability to perform the procedure. Once the turbinate has been reduced, aeration and drainage are reestablished to allow the sinuses to heal and return to their normal function.

Depending on the procedure, the surgeon may rotate and/or translate the staple electrodes 105 relative to the turbinate tissue to form holes, channels, stripes, divots, craters or the like within the turbinate. In addition, the surgeon may purposely create some thermal damage within these holes, or channels to form scar tissue that will inhibit the turbinate from swelling after the procedure. In one embodiment, the physician axially rotates the shaft distal portion 120 within the turbinate tissue as the tissue is volumetrically removed to form one or more holes in the turbinate, typically having a diameter of less than 5 mm, preferably less than 2 mm. The active electrode 104 may be generally sized to be approximately the length of an average body structure to be treated. For example a turbinate may typically be approximately 10-15 mm long and an active electrode 105 may be approximately 5-20 mm in length, to accommodate the particular target turbinate. Instrument 90 and active electrode length is operable to treat tissue during a predominantly rotational movement with minimal advancing and retracting. This allows the surgeon to plan for a more reliable amount of removed or treated tissue. In another embodiment, the physician may also axially translate the distal portion 120 into the turbinate tissue as the tissue is volumetrically removed to form one or more holes in the turbinate, typically having a diameter of less than 2 mm, preferably less than 1 mm. Shaft distal portion 120 may be sized so as to access the nasal cavity and form these holes, and therefore would be between 1-5 mm in diameter and more preferably approximately 2 mm. In another embodiment, the physician may translate the staple electrode 105 across the outer surface of the turbinates to form one or more channels or troughs. Applicant has found that the present invention can quickly and cleanly create such holes, divots or channels in tissue with the cold ablation technology described herein.

Another advantage of the present invention is the ability to precisely ablate channels or holes within the turbinates without causing necrosis or thermal damage to the underlying and surrounding tissues, nerves (e.g., the optic nerve) or bone. In addition, the voltage can be controlled so that the energy directed to the target site is insufficient to ablate bone or adipose tissue (which generally has a higher impedance than the target sinus tissue). In this manner, the surgeon can literally clean the tissue off the bone, without ablating or otherwise effecting significant damage to the bone.

Figure 4:
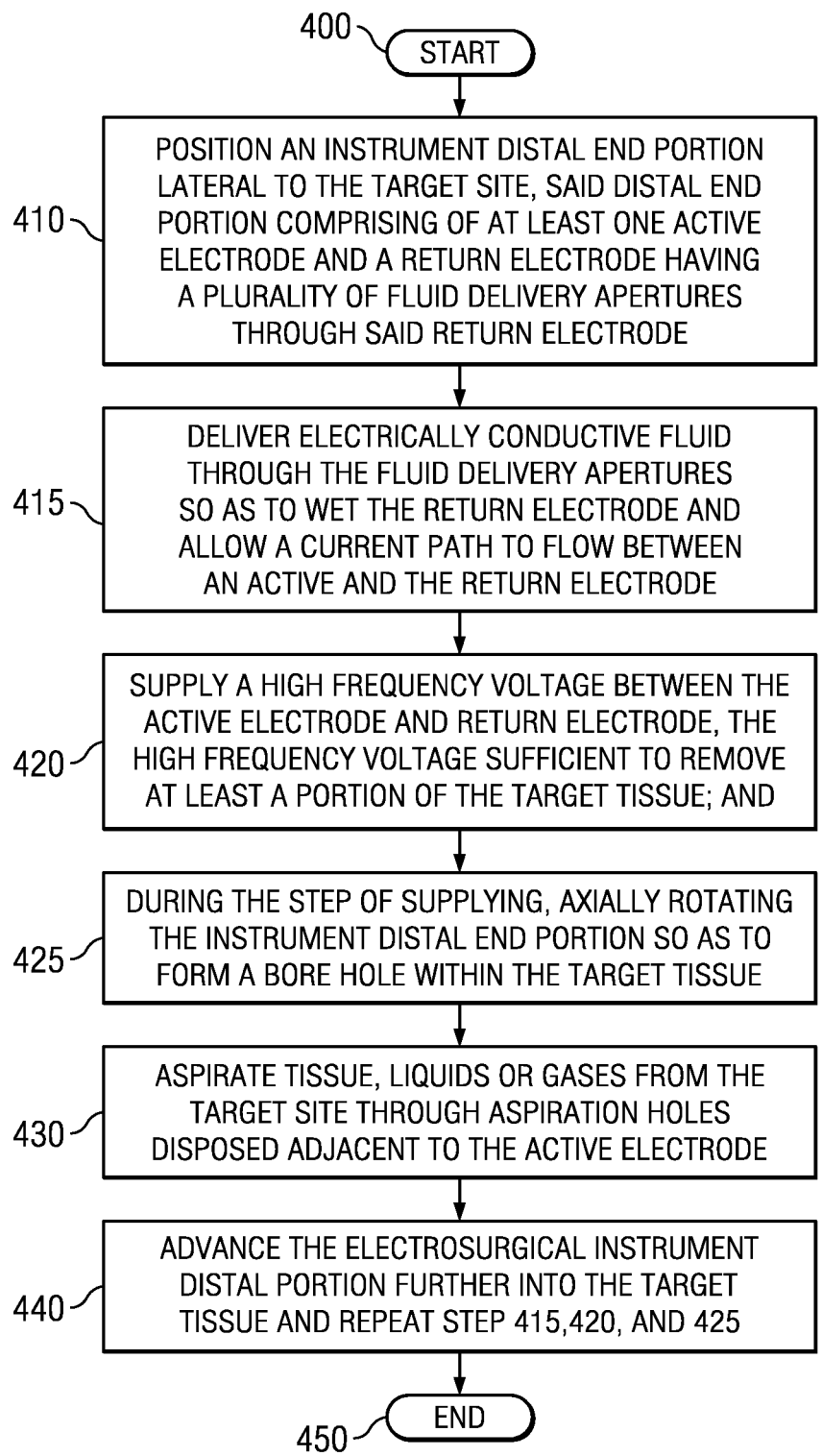
FIG. 4 shows a flow diagram of a medical procedure, using a system according to at least certain embodiments.

Referring now to FIG. 4, a method (400) for treating tissue in accordance with at least some of the embodiments described herein is illustrated, including the steps of: positioning an instrument distal end portion lateral to the target site, said distal end portion comprising at least one active electrode and a return electrode having at plurality of fluid delivery apertures through said return electrode (410). Electrically conductive fluid may then be delivered (415) through the fluid delivery apertures via a fluid delivery element, so as to wet the return electrode and create a fluid bridge between the active and return electrode, to allow a current path to flow between an active and the return electrode followed by supplying a high frequency voltage between the active electrode and return electrode, the high frequency voltage sufficient to remove at least a portion of the target tissue (420). During the step of supplying, the instrument distal end may then be rotated so as to form a bore hole within the target tissue (425). Tissue, liquids or gases may be aspirated from the target site though aspiration holes disposed adjacent to the active electrode (430).

The electrosurgical instrument distal may be advanced further into the target tissue at this point (440) and the treatment repeated as described above. The tissue may comprise a blockage within the nasal cavity or a paranasal sinus of the patient and the blockage may be from the group comprising swollen tissue, turbinates, polyps, neoplasms and swollen mucus membranes lining an inner surface of the nasal cavity. Other tissues outside of the nasal cavity may also be treated, such as prostate, heart or any other body structure. The high frequency voltage may be altered or sufficient as is to effect hemostasis of severed blood vessels within the tissue during the supplying step. The electrosurgical probe may further comprise a distal tip, operable to bluntly dissect tissue or create a window into a body structure.

Although only a few embodiments of the present invention have been described, it should be understood that the present invention may be embodied in many other specific forms without departing from the spirit or the scope of the present invention. Therefore, the present examples are to be considered as illustrative and not restrictive, and the invention is not to be limited to the details given herein, but may be modified within the scope of the appended claims.

What is claimed is:

1. An electrosurgical apparatus for treating tissue at a target site comprising:
   a shaft that defines a proximal end and a distal portion;
   at least one active electrode disposed on the distal portion of the shaft;
   a return electrode defining at least a portion of the distal portion of the shaft, the return electrode at least partially encircling an electrode insulator and having an outer surface;
   a plurality of discharge apertures through the return electrode, the plurality of discharge apertures fluidly connected to a fluid delivery element within shaft, the fluid delivery element to deliver an electrically conductive fluid through the plurality of discharge apertures laterally disposed and transverse to the at least one active electrode; and a plurality of aspiration apertures disposed through the electrode insulator and directly adjacent to the at least one active electrode, the plurality of aspiration apertures spaced away from the plurality of discharge apertures so as to direct the electrically conductive fluid from the plurality of discharge apertures to uniformly wet the outer surface before flowing into the plurality of aspiration apertures.

2. The electrosurgical apparatus of claim 1 wherein the fluid delivery element comprises at least one fluid delivery lumen extending within at least a portion of the shaft length and defined by an inner surface of the shaft, wherein the fluid delivery element has an inlet proximal to the shaft proximal end.

3. The electrosurgical apparatus of claim 2 wherein the at least one fluid delivery lumen comprises at least one annular space between the return electrode and the electrode insulator, wherein the at least one annular space is in fluid communication with the plurality of discharge apertures.

4. The electrosurgical apparatus of claim 3, wherein the plurality of aspiration apertures are fluidly connected to an aspiration element comprising at least one aspiration lumen extending within at least a portion of the electrode insulator and wherein the at least one aspiration lumen has an outlet proximal to proximal end of the electrode insulator.

5. The electrosurgical apparatus of claim 1, wherein the plurality of discharge apertures comprise at least one row of axially spaced discharge apertures disposed laterally through the shaft distal portion.

6. The electrosurgical apparatus of claim 1, wherein the return electrode has at least one opening, wherein the at least one active electrode is disposed within at least one opening.

7. The electrosurgical apparatus of claim 6 wherein the return electrode opening has an edge, and wherein the shortest distance between the opening edge and an adjacent active electrode is approximately equal along the length of the opening edge.

8. The electrosurgical apparatus of claim 1 wherein the at least one active electrode comprises an electrode array.

9. The electrosurgical apparatus of claim 8, wherein the electrode array comprises a row of staple shaped electrodes.

10. The electrosurgical apparatus of claim 1, wherein the at least one active electrode bridges at least one of the plurality of aspiration apertures.

11. The electrosurgical apparatus of claim 1, further comprising a distal tip comprising a leading edge, wherein the leading edge is operable to dissect tissue adjacent the target tissue.

12. The electrosurgical apparatus of claim 1 wherein the return electrode encircles a portion of the electrode insulator and at least partially encircles at least one active electrode and extends distally and proximally relative to the active electrode.

13. The electrosurgical apparatus of claim 1 wherein the electrically conductive fluid from the plurality of discharge apertures to uniformly wet the outer surface creates a wetted return electrode surface area, wherein the ratio of wetted return electrode surface area to active electrode surface area is between 2:1 and 10:1.

14. The electrosurgical apparatus of claim 1 wherein the distal portion is sized for delivery into a paranasal cavity of a patient.

15. The electrosurgical apparatus of claim 1 wherein the apparatus is operable to treat tissue selected from a group consisting of polyps, turbinatem neoplasms, or swollen mucous membranes.

16. The electrosurgical apparatus of claim 1 wherein the at least one active electrode comprises a loop of wire.

17. The electrosurgical apparatus of claim 1, further comprising a connector disposed at the proximal end for electrically coupling the at least one active electrode and the return electrode to a high frequency power supply.

18. An electrosurgical apparatus for removing tissue from a body structure comprising:

a shaft having a proximal end and a distal portion and a distal tip, wherein the shaft distal portion defines a return electrode encircling a insulator member, the insulator member having a distal tip extending beyond the distal portion;

at least one active electrode secured on the insulator member;

a plurality of discharge apertures through the return electrode, the plurality of apertures fluidly connected to a fluid delivery lumen within the shaft and disposed laterally to the at least one active electrode, the fluid delivery lumen defined by at least one annular space between the return electrode and the insulator member and fluidly connected with the plurality of discharge apertures, the at least one annular space adapted to allow a flow of a conductive fluid to discharge through the plurality of discharge apertures so that the conductive fluid may only reach the at least one active electrode having traversed a substantial portion of an outer surface of the return electrode first, thereby uniformly wetting the outer surface.

19. The electrosurgical apparatus of claim 18, wherein the plurality of discharge apertures are arranged in at least one row of axially spaced apertures disposed laterally on the shaft distal portion.

20. The electrosurgical apparatus of claim 18, wherein the fluid delivery lumen is fluidly connected to a fluid delivery element containing an electrically conductive fluid.

21. The electrosurgical apparatus of claim 20, wherein the conductive fluid creates a wetted return electrode surface area, and wherein the ratio of wetted return electrode surface area to an active electrode surface area is between 2:1 and 10:1.

22. The electrosurgical apparatus of claim 18, further comprising a connector disposed at the proximal end for electrically coupling the at least one active electrode and the return electrode to a high frequency power supply.

23. The electrosurgical apparatus of claim 18 wherein the at least one active electrode comprises an electrode array.

24. The electrosurgical apparatus of claim 23, wherein the electrode array comprises a row of staple shaped electrodes.

25. The electrosurgical apparatus of claim 18 further comprising at least one aspiration aperture disposed through the insulator member and fluidly connected to an aspiration element, comprising at least one aspiration lumen extending within at least a portion of the tubular insulator member and wherein the at least one aspiration lumen has an outlet proximal to a proximal end of the insulator member.

26. The electrosurgical apparatus of claim 25, wherein the at least one aspiration aperture is disposed adjacent the at least one active electrode.

27. The electrosurgical apparatus of claim 18, wherein the distal tip comprises a leading edge, operable to bluntly dissect body tissue and create a window into the body structure.

28. The electrosurgical apparatus of claim 18, wherein the return electrode has at least one opening, wherein the at least one active electrode is disposed within the at least one opening.

29. The electrosurgical apparatus of claim 18 wherein the tubular insulator member comprises a working surface supporting the at least one active electrode, and wherein the working surface has a standoff distance from the return electrode between and including 0.010 inches and 0.025 inches.

30. An electrosurgical system for treating tissue of a body structure comprising:
- an electrosurgical controller, the electrosurgical controller configured to produce radio frequency (RF) energy at an active terminal with respect to a return terminal;
- an electrosurgical wand coupled to the electrosurgical controller, the electrosurgical wand comprising:
- an elongate shaft having a proximal end, a distal portion and a distal tip;
- at least one active electrode disposed on the distal portion of the shaft, the at least one active electrode electrically coupled to the active terminal;
- a return electrode defining a portion of the distal portion of the shaft, the return electrode partially encircling an insulating member, the return electrode electrically coupled to the return terminal;
- a plurality of discharge apertures through the return electrode, the plurality of apertures fluidly connected to a fluid delivery element within shaft, the plurality of discharge apertures disposed transverse to the at least one active electrode;
- a plurality of aspiration apertures disposed on the distal portion of the shaft and fluidly connected with an aspiration elements disposed within the shaft, the aspiration apertures directly adjacent to the at least one active electrode; and
- wherein the insulating member defines both a portion of the aspiration element, and in cooperation with the return electrode defines a portion of the fluid delivery element.

* * * * *